(12) United States Patent
Fomina et al.

(10) Patent No.: US 11,814,675 B2
(45) Date of Patent: Nov. 14, 2023

(54) EDGE SEQUENCING WITH AN IMMOBILIZED TRANSLOCATOR

(71) Applicant: Robert Bosch GmbH, Stuttgart (DE)

(72) Inventors: Nadezda Fomina, Redwood City, CA (US); Christopher Johnson, San Carlos, CA (US); Young Shik Shin, Mountain View, CA (US); Christoph Lang, Sunnyvale, CA (US)

(73) Assignee: Robert Bosch GmbH, Stuttgart (DE)

( * ) Notice: Subject to any disclaimer, the term of this patent is extended or adjusted under 35 U.S.C. 154(b) by 934 days.

(21) Appl. No.: 16/555,924

(22) Filed: Aug. 29, 2019

(65) Prior Publication Data

US 2021/0062255 A1 Mar. 4, 2021

(51) Int. Cl.
*G01N 27/30* (2006.01)
*G01N 27/327* (2006.01)
*G01N 33/52* (2006.01)
*C12Q 1/6869* (2018.01)
*B01L 3/00* (2006.01)
*B01J 19/00* (2006.01)

(52) U.S. Cl.
CPC ........ *C12Q 1/6869* (2013.01); *B01J 19/0093* (2013.01); *B01L 3/502715* (2013.01);
(Continued)

(58) Field of Classification Search
CPC ......... G01N 27/44791; G01N 27/4473; G01N 27/48707; G01N 27/4873;
(Continued)

(56) References Cited

U.S. PATENT DOCUMENTS 9,347,900 B2 5/2016 Korlach et al.
9,988,678 B2 6/2018 Lee et al.
(Continued)

FOREIGN PATENT DOCUMENTS

DE 102013010961 1/2015

OTHER PUBLICATIONS

Emaminejad, S. et al., "Tunable control of antibody immobilization using electric field," Proceedings of the National Academy of Science, 112.7 (2015), pp. 1995-1999.
(Continued)

*Primary Examiner* — Gurpreet Kaur
(74) *Attorney, Agent, or Firm* — Brooks Kushman P.C.

(57) ABSTRACT

The present disclosure relates to systems, devices, and methods for nucleic acid sequencing including polynucleotide strands having a nucleotide(s) modified with a redox label(s) attached thereto or capable of receiving the modified nucleotide(s) with a redox label(s) attached thereto. The systems, devices, and methods include a dielectric member with an attached translocating protein positioned between oxidizing and reducing electrodes. The oxidizing and reducing electrodes generate an electrical field extending to a reaction area where the translocation of the polynucleotide strand through the protein occurs such the modified nucleotide(s) with redox label(s) attached thereto are identified by changes in current flow in the oxidizing and reducing electrodes, wherein the changes identify electron transfer from the reducing electrode, to redox label, and to oxidizing electrode when the modified nucleotide with a redox label covalently bonded to the nucleoside base of the modified nucleotide of the polynucleotide strand is at the reaction area.

22 Claims, 19 Drawing Sheets

Specification includes a Sequence Listing.

(52) U.S. Cl.
CPC ....... *G01N 27/307* (2013.01); *G01N 27/3272* (2013.01); *G01N 27/3275* (2013.01); *G01N 33/526* (2013.01); *B01L 2300/0645* (2013.01)

(58) Field of Classification Search
CPC ....... G01N 33/48721; G01N 33/48728; G01N 33/68; C12Q 1/6869; C12Q 1/6825; C12Q 1/68; C12Q 1/6813; C12Q 1/6876; C12Q 2563/116; C12Q 2565/631; Y10S 977/852; Y10S 977/733; Y10S 977/72; Y10S 977/721
See application file for complete search history.

(56) References Cited

U.S. PATENT DOCUMENTS

| | | | |
|---|---|---|---|
| 2009/0170716 A1* | 7/2009 | Su | C12Q 1/6869 435/6.16 |
| 2013/0109577 A1* | 5/2013 | Korlach | G01N 27/3278 506/13 |
| 2015/0132756 A1* | 5/2015 | Peter | C12Q 1/6869 435/6.11 |
| 2017/0370870 A1 | 12/2017 | Fomina et al. | |
| 2019/0137435 A1 | 5/2019 | Johnson et al. | |

OTHER PUBLICATIONS

Jung, S.E. et al., "Surface modification of aluminum oxide for biosensing application," Biomedical Engineering: Applications, Basis and Communications, 24.02 (2012), pp. 111-116.

Mutin, P.H. et al., "Selective surface modification of SiO2—TiO2 supports with phosphonic acids," Chemistry of Materials 16.26 (2004), pp. 5670-5675.

Verma, S. et al., "Modified Oligonucleotides: Synthesis and Strategy for Users," Annu. Rev. Biochem. (1998), 67:\, pp. 99-134.

* cited by examiner

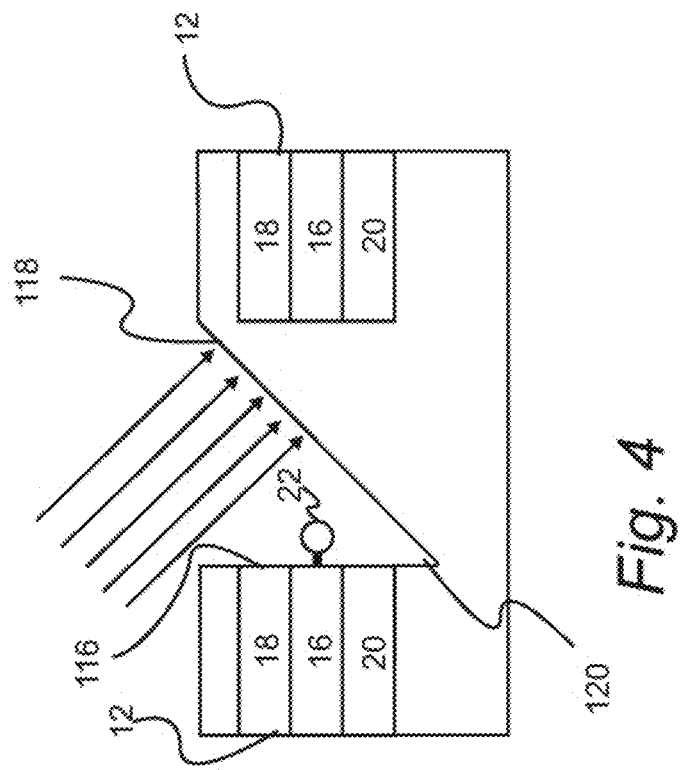
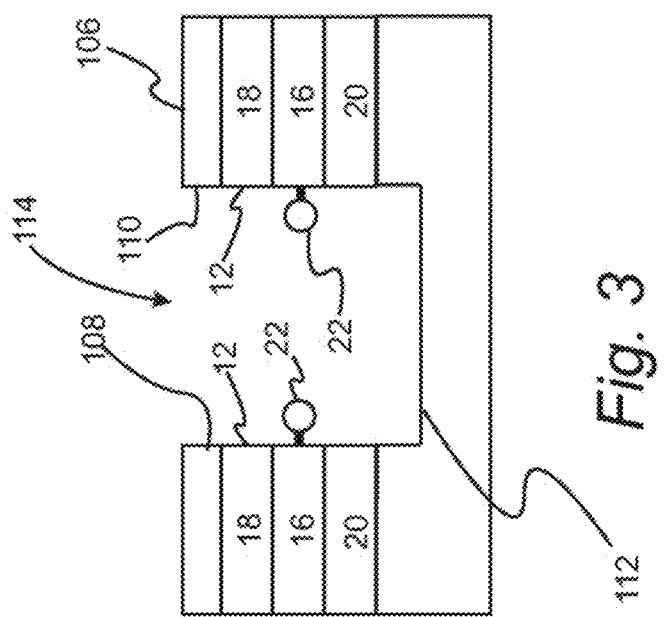
Fig. 4
Fig. 3

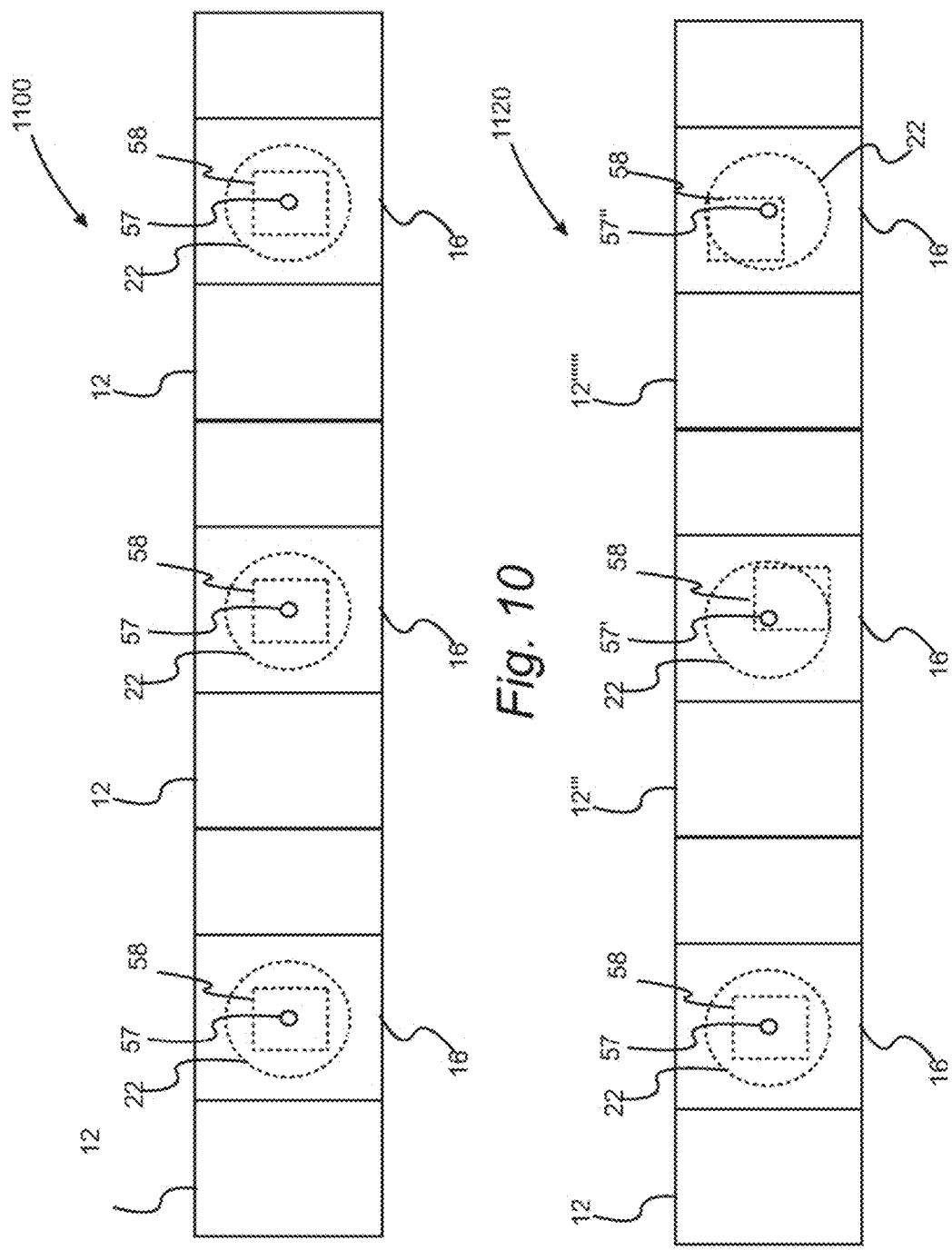

EDGE SEQUENCING WITH AN IMMOBILIZED TRANSLOCATOR

SEQUENCE LISTING

The text file edge_ST25 of size 1 KB created Nov. 8, 2019 filed herewith, is hereby incorporated by reference.

TECHNICAL FIELD

In at least one aspect, the present disclosure relates to systems, devices, and methods for nucleic acid sequencing.

BACKGROUND

Single base resolution DNA sequencing is a significant goal within biotechnology. To date, the majority of techniques require either significant rebuilding of the sequence from small reads or repeated runs to achieve fidelity.

SUMMARY

The present disclosure solves one or more problems of the prior art by disclosing systems, devices, and methods for nucleic acid sequencing which sequence polynucleotide strands such as long reads with single base pair resolution. The benefit of this modality is the translocating protein acts as a controlled localization site to bring the polynucleotide strands into a sensing zone and at the same time provides a controlled rate of translocation within the sensing zone.

In another aspect, a system for nucleic acid sequencing is provided. The system includes at least one device that includes an oxidizing electrode, a reducing electrode, and a dielectric member positioned between the oxidizing electrode and reducing electrode. Characteristically, the dielectric member separates the reducing electrode from the oxidizing electrode by a first distance of at most 10 nm. A protein is attached to the surface of the dielectric member. The protein is capable of translocating a polynucleotide strand having a nucleotide modified with a redox label or capable of receiving the modified nucleotide with a redox label covalently bonded to the nucleoside base of the modified nucleotide. The attachment of the protein is such that the modified nucleotide with a redox label covalently bonded to the nucleoside base of the modified nucleotide of the polynucleotide strand passes to within a second distance that is at most 10 nanometer (nm) from the surface of the dielectric member during translocation. The oxidizing and reducing electrodes generate an electric field that extends to a reaction area where the translocation of the polynucleotide strand through the protein occurs. Advantageously, the spatial dimensions allow a rapid electron transfer (i.e., nearly simultaneously) from the reducing electrode to redox label to the oxidizing electrode when the modified nucleotide with a redox label covalently bonded to the nucleoside base of the modified nucleotide is located at the reaction area.

In another aspect, a method for forming nucleic acid sequencing devices is provided. The method includes a first step of providing a device including an oxidizing electrode, a reducing electrode, and a dielectric member. Characteristically, the dielectric member separates the reducing electrode from the oxidizing electrode by a first distance of at most 10 nm. The method includes a second step of generating an electric field by the oxidizing electrode, the reducing electrode, or both. The method also includes a third step of attaching a protein to a surface of the dielectric member. The protein is capable of translocating a polynucleotide strand having a nucleotide modified with a redox label or capable of receiving the modified nucleotide with a redox label covalently bonded to the nucleoside base of the modified nucleotide to a surface of the dielectric member. The protein is attached to the surface of the dielectric member such that the modified nucleotide with a redox label covalently bonded to the nucleoside base of the modified nucleotide of the polynucleotide strand passes at most 10 nm from the surface of the dielectric member during translocation. The method allows for the fabrication of arrays including devices with translocating proteins that are at least partially aligned on the surfaces of the dielectric members and optionally, uniformly distributed. Advantageously, this allows for a stronger signal when changes in current flow are detected.

In still another aspect, a method for nucleic acid sequencing is provided. The method includes a first step of providing at least one device including an oxidizing electrode, a reducing electrode, a dielectric member, and a protein attached to a surface of the dielectric member. Characteristically, the dielectric member separates the reducing electrode from the oxidizing electrode by a first distance of at most 10 nm. The protein is capable of translocating a polynucleotide strand having a nucleotide modified with a redox label or capable of receiving the modified nucleotide with a redox label covalently bonded to the nucleoside base of the modified nucleotide. The attachment of the protein is such that the modified nucleotide with a redox label covalently bonded to the nucleoside base of the modified nucleotide of the polynucleotide strand passes to within a second distance that is at most 10 nm from the surface of the dielectric member during translocation. The method includes a third step of directing current through the oxidizing and reducing electrodes, where the oxidizing and reducing electrodes generate an electric field that extends to a reaction area where the translocation of the polynucleotide strand through the protein occurs. The method includes a fourth step of exposing the protein to a sample including the polynucleotide strand that allows for the polynucleotide strand to be translocated through the protein. The method includes a fifth step of detecting changes in current flow in the oxidizing and reducing electrodes. The changes identify electron transfer from the reducing electrode, to redox label, and to oxidizing electrode when the modified nucleotide with a redox label covalently bonded to the nucleoside base of the modified nucleotide of the polynucleotide strand is at the reaction area. Advantageously, the spatial dimensions allow a rapid electron transfer (i.e., nearly simultaneously) from the reducing electrode to redox label to the oxidizing electrode when the modified nucleotide with a redox label covalently bonded to the nucleoside base of the modified nucleotide is located at the reaction area.

BRIEF DESCRIPTION OF THE DRAWN

For a further understanding of the nature, objects, and advantages of the present disclosure, reference should be had to the following detailed description, read in conjunction with the following drawings, wherein like reference numerals denote like elements and wherein:

FIGS. 3 and 4 show schematics of two different geometries of a non-planar design, where the electrode pairs are fabricated as a stack in a well format and the well is filled on one side.

FIG. 10 shows a system including, three devices.

FIG. 11 shows a system including three devices

Figure 13:
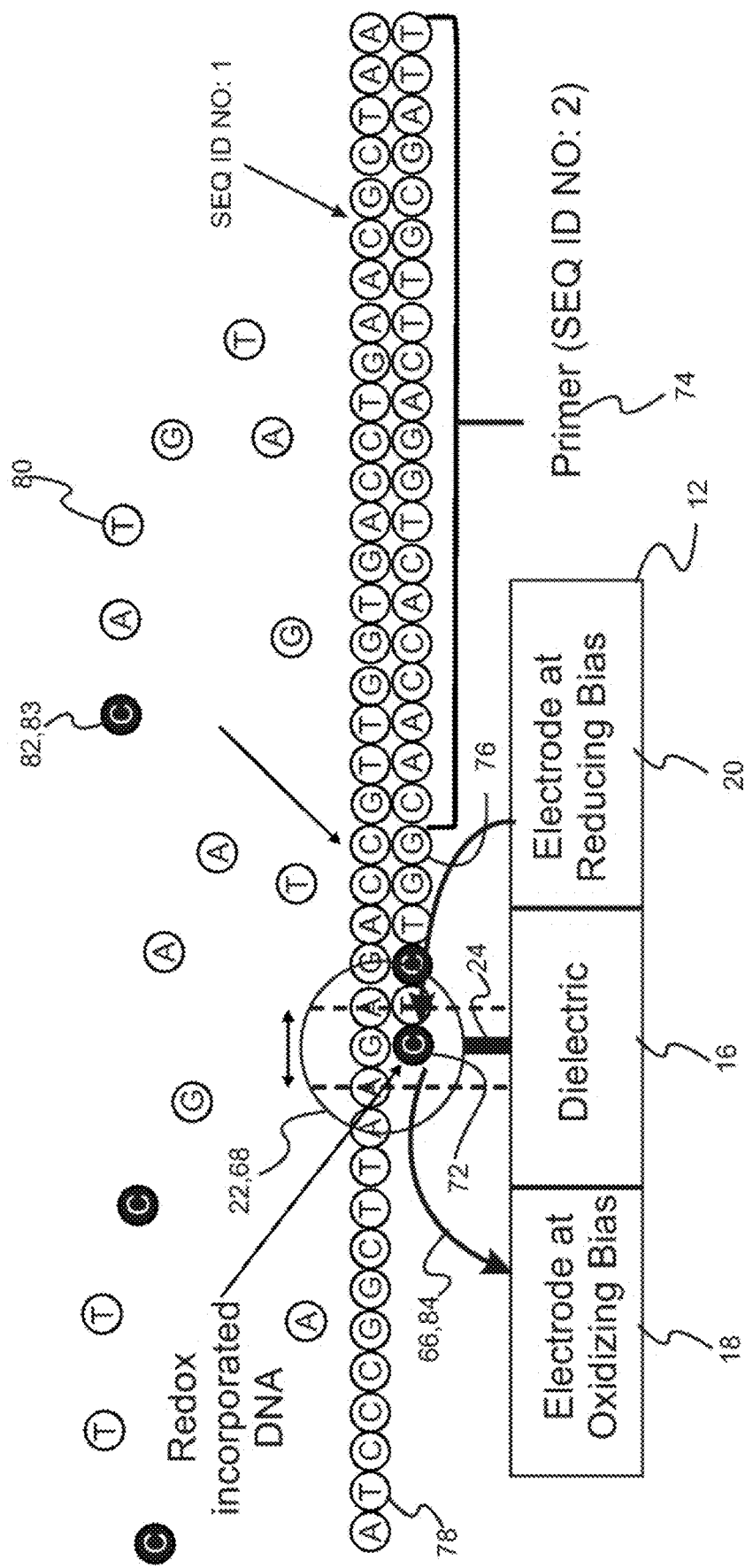

FIG. 13 is a schematic of a method for polymerase mediated redox DNA sequencing. The polymerase is anchored to the surface of a rim scale dielectric between 2 electrodes. The polymerase can bind with a DNA and primer strand and start incorporating nucleotides via the polymerase chain reaction. As disclosed in FIG. 13, the shaded. C bases represent redox modified. Cytosine nucleotides that can undergo oxidation and reduction reactions with the adjacent electrodes within the sensing zone. The probing of the redox modified nucleotide with a redox label covalently bonded to the nucleoside base of the modified nucleotide as they get incorporated can be used to determine the DNA sequence of the strand.

Figure 14:
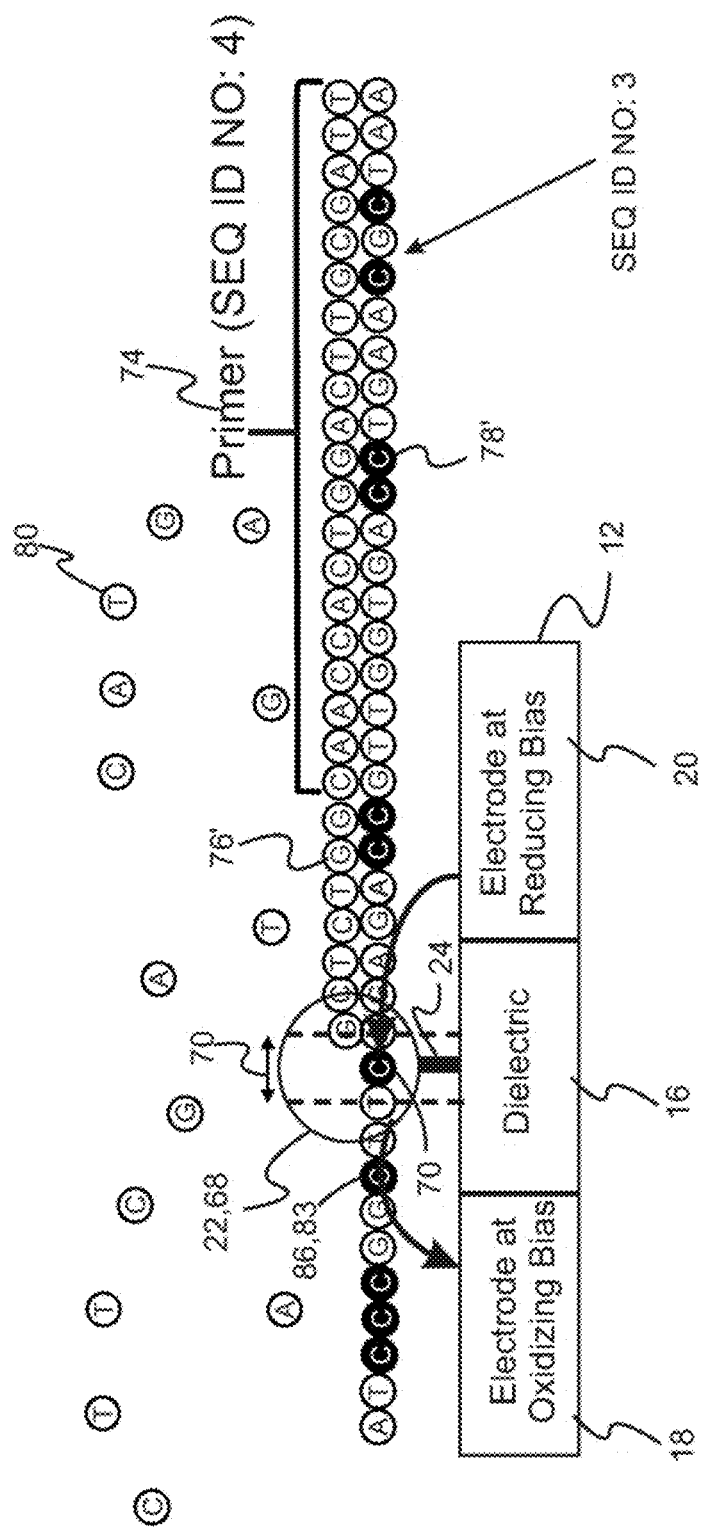

FIG. 14 is a schematic of an alternate method for polymerase mediated redox DNA sequencing. The polymerase is anchored to the surface of a nm scale dielectric between 2 electrodes. The polymerase can bind with a DNA and primer strand and start incorporating nucleotides via the polymerase chain reaction. In this example, the shaded species along the strand represent redox modified cytosine nucleotides, which can undergo oxidation and reduction reactions with the adjacent electrodes within the sensing zone. The probing of the redox modified nucleotide with a redox label covalently bonded to the nucleoside base of the modified nucleotide previously incorporated in the DNA can be used to determine the DNA sequence of the strand.

Figure 15:
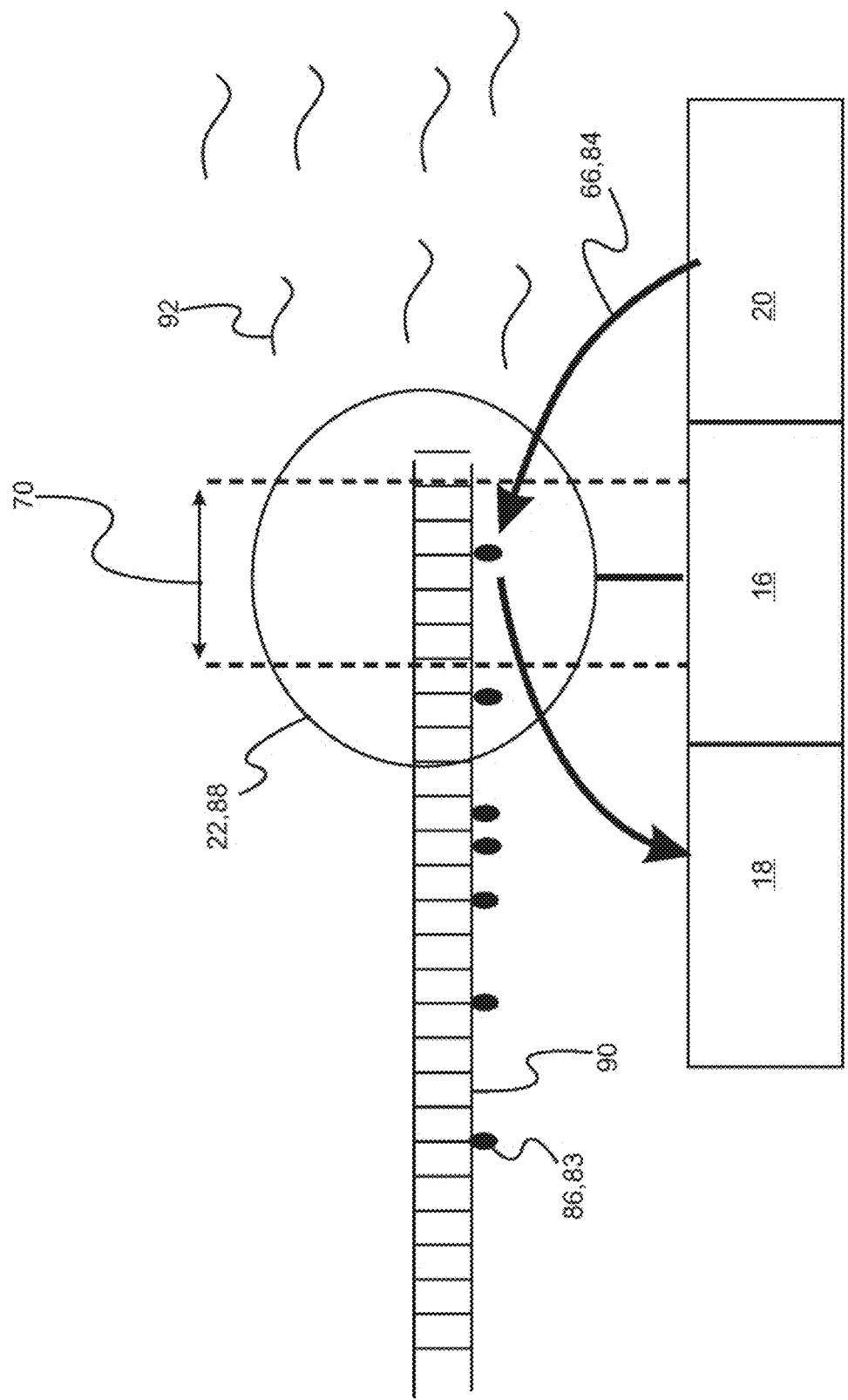
Figure 16:
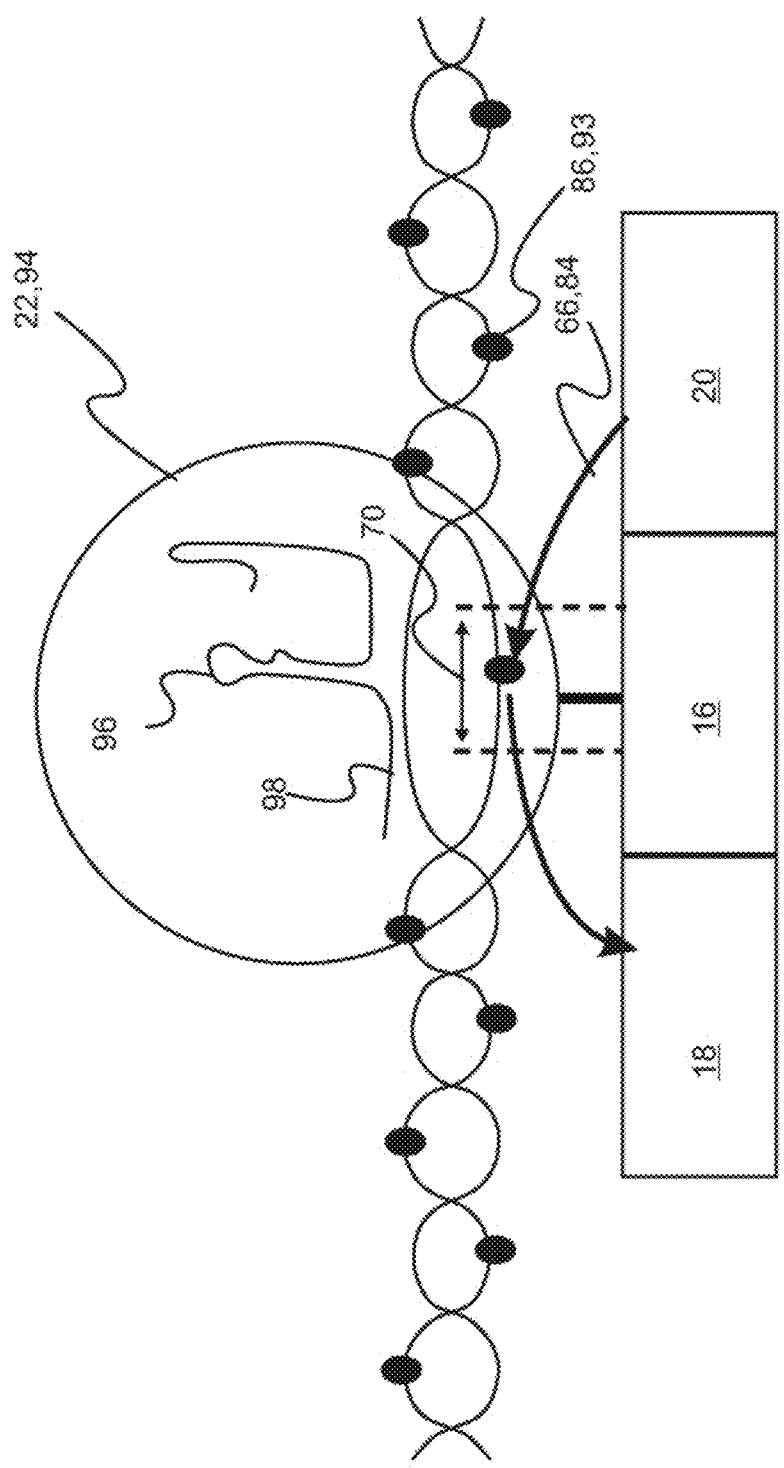

FIGS. 15 and 16 show methods and systems of nucleic acid sequencing.

Figure 17:
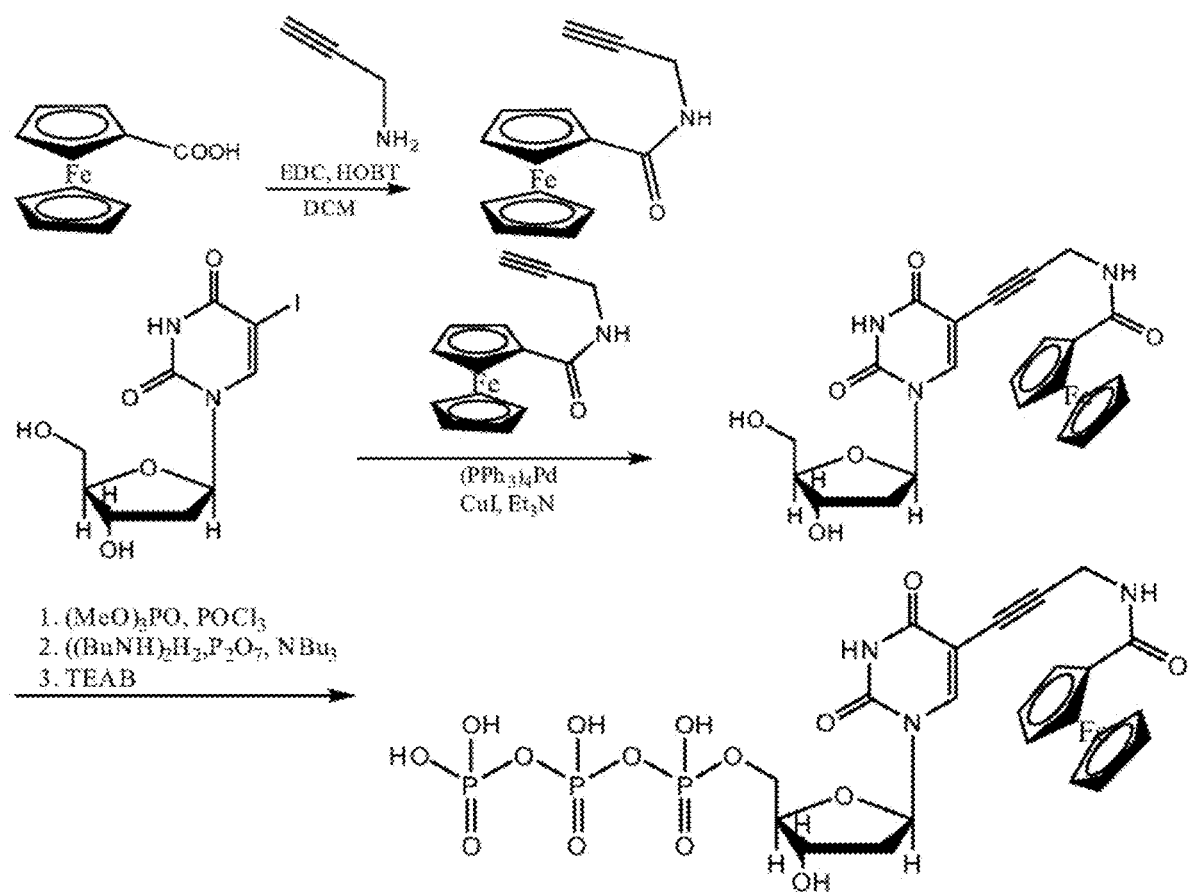

FIG. 17 shows a synthetic route to generate a redox modified nucleotide with a redox label covalently bonded to the nucleoside base of the modified nucleotide.

Figure 18:
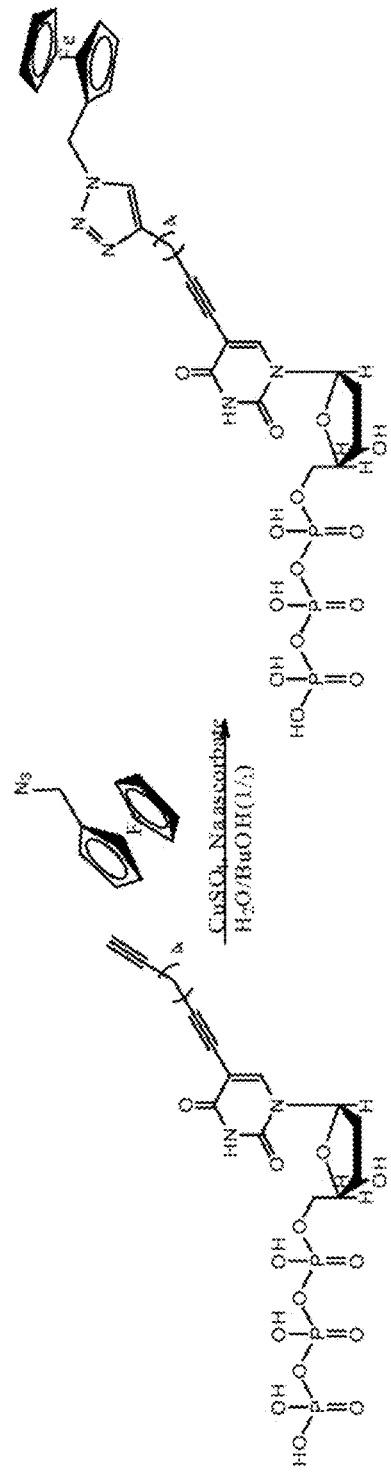

FIG. 18 shows a synthetic route for "Click" mediated redox modification of a single nucleotide.

Figure 19:
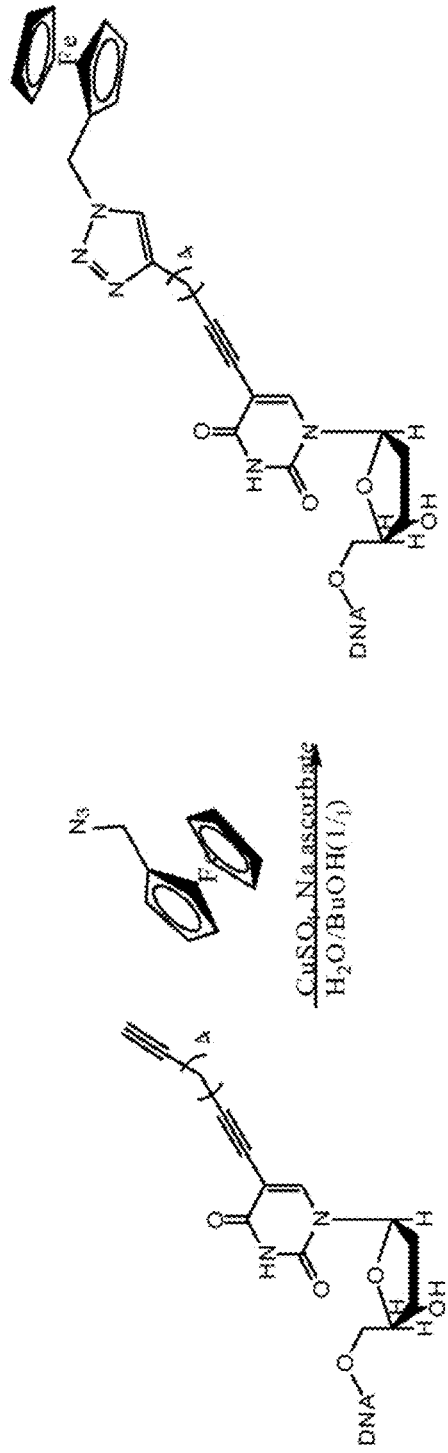

FIG. 19 shows a synthetic route for "Click" mediated redox modification of an incorporated nucleotide.

DETAILED DESCRIPTION

As required, detailed embodiments of the present disclosure are disclosed herein; however, it is to be understood that the disclosed embodiments are merely exemplary and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art.

Except in the examples, or where otherwise expressly indicated, all numerical quantities in this description indicating amounts of material or conditions of reaction and or use are to be understood as modified by the word "about". The first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

Unless indicated otherwise, all technical and scientific terms used herein have the same meaning as commonly understood by one of ordinary skill in the art to which the present disclosure belongs.

It is also to be understood that this disclosure is not limited to the specific embodiments and methods described below, as specific components and/or conditions may, of course, vary. Furthermore, the terminology used herein is used only for describing particular embodiments and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The terms "or" and "and" can be used interchangeably and can be understood to mean "and/or".

The term "comprising" is synonymous with "including," "having," "containing," or "characterized by." These terms are inclusive and open-ended and do not exclude additional unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

The terms "polynucleotide", "nucleotide", "nucleotide sequence", "nucleic acid" and "oligonucleotide" are used interchangeably in this disclosure. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense)

and double-stranded polynucleotides. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "sequence identity" or "identity" refers to a specified percentage of residues in two nucleic acid or amino acid sequences that are identical when aligned for maximum correspondence over a specified comparison window, as measured by sequence comparison algorithms or by visual inspection. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity.

The term "comparison window" refers to a segment of at least about 20 contiguous positions in which a sequence may be compared to a reference sequence of the same number of contiguous positions after the two sequences are aligned optimally. In a refinement, the comparison window is from 15 to 30 contiguous positions in which a sequence may be compared to a reference sequence of the same number of contiguous positions after the two sequences are aligned optimally. In another refinement, the comparison window is usually from about 50 to about 200 contiguous positions in which a sequence may be compared to a reference sequence of the same number of contiguous positions after the two sequences are aligned optimally.

The terms "complementarity" or "complement" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 4, 5, and 6 out of 6 being 66.67%, 83.33%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 40%, 50%, 60%, 62.5%, 70%, 75%, 80%, 85%, 90%, 95%, 97%, 98%, 99%, or 100%, or percentages in between over a region of 4, 5, 6, 7, and 8 nucleotides, or refers to two nucleic acids that hybridize under stringent conditions.

The term "translocator", "translocating protein", "enzyme", and "protein" as used herein refers to any peptide, oligopeptide, polypeptide, gene product, expression product, or protein capable of translocating a polynucleotide strand. Examples of proteins capable of translocating a polynucleotide strand include DNA polymerase, RNA polymerase, ribosome, a single-stranded binding protein, topoisomerase, helicase, nuclease, exonuclease, endonuclease, a zinc finger nuclease, an RNA guided DNA endonuclease, a transcription activator-like effector nuclease, a CRISPR protein, and combinations thereof.

Unless expressly stated to the contrary: all R groups (e.g. $R_i$ where i is an integer) include hydrogen, alkyl, lower alkyl, $C_{1-6}$ alkyl, $C_{6-10}$ aryl, $C_{6-10}$ heteroaryl, —$NO_2$, —$NH_2$, —$N(R'R'')_2$, $N(R'R''R''')_3^{+L^-}$, Cl, F, Br, —$CF_3$, —$CCl_3$, —CN, —$SO_3H$, $PO_3H_2$, —COOH, —$CO_2R'$, —$COR'$, —CHO, —OH, —OR', —$O^-M^+$, —$SO_3^-M^+$, —$PO_3^-M^+$, —$COO^-M^+$, —$CF_2H$, —$CF_2R'$, —$CFH_2$, and —CFR'R" where R', R" and R''' are $C_{1-10}$ alkyl or $C_{6-18}$ aryl groups; single letters (e.g., "n" or "o") are 1, 2, 3, 4, or 5; in the compounds disclosed herein a CH bond can be substituted with alkyl, lower alkyl, $C_{1-6}$ alkyl, $C_{6-10}$ aryl, $C_{6-10}$ heteroaryl, —$NO_2$, —$N(R'R')_2$, —$N(R'R''R''')_3^{+L^-}$, Cl, F, Br, —$CF_3$, —$CCl_3$, —CN, —$SO_3H$, —$PO_3H_2$, —COOH, —CHO, —OH, —OR', —$O^-M^+$, —$SO_3^-M^+$, —$PO_3^-M^+$, —$COO^-M^+$, —$CF_2H$, —$CF_2R'$, and —$CFH_2$, where R', R" and R''' are $C_{1-10}$ alkyl or $C_{6-18}$ aryl groups; the indication of a moiety or structure with positive charges implies that one or more negative counter ions are present to balance the charge, similarly, the indication of a moiety or structure with negative charges implies that one or more positive counter ions are present to balance the charge; percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

The term "alkyl" as used herein means $C_{1-20}$, linear, branched, rings, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. Lower alkyl can also refer to a range between any two numbers of carbon atoms listed above. "Higher alkyl" refers to an alkyl group having about 10 to about 20 carbon atoms, e.g., 10, 11, 12, 13, 14, 15, 16, 17, 18, 19, or 20 carbon atoms. Higher alkyl can also refer to a range between any two number of carbon atoms listed above.

The term "aryl" as used herein means an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Examples of aryl include, but are not limited to, phenyl, naphthyl, biphenyl, and diphenylether, and the like. Aryl groups include heteroaryl groups, wherein the aromatic ring or rings include a heteroatom (e.g., N, O, S, or Se). Exemplary heteroaryl groups include, but are not limited to, furanyl, pyridyl, pyrimidinyl, imidazoyl, benzimidazolyl, benzofuranyl, benzothiophenyl, quinolinyl, isoquinolinyl, thiophenyl, and the like. The aryl group can be optionally substituted (a "substituted aryl") with one or more aryl group substituents, which can be the same or different, wherein "aryl group substituent" includes alkyl (saturated or unsaturated), substituted alkyl (e.g., haloalkyl and perhaloalkyl, such as but not limited to —$CF_3$), cycloalkyl, aryl, substituted aryl, aralkyl, halo, nitro, hydroxyl, acyl, carboxyl, alkoxyl (e.g., methoxy), aryloxyl, aralkyloxyl, thioalkyl, thioaryl, thioaralkyl, amino (e.g., aminoalkyl, aminodialkyl, aminoaryl, etc.), sulfonyl and sulfinyl.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits. In the specific examples set forth herein, concentrations, temperature, and reaction conditions (e.g. pressure, pH, etc.) can be practiced with plus or minus 50 percent of the values indicated rounded to three significant figures. In a refinement, concentrations, temperature, and reaction conditions (e.g., pressure, pH, etc.) can be practiced with plus or minus 30 percent of the values indicated rounded to three significant figures of the value provided in the examples. In another refinement, concentrations, temperature, and reaction conditions (e.g., pH, etc.) can be practiced with plus or minus 10 percent of the values indicated rounded to three significant figures of the value provided in the examples.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

Throughout this application, where publications are referenced, the disclosures of these publications in their entireties are hereby incorporated by reference into this application to more fully describe the state of the art to which this invention pertains.

The present disclosure discloses a device that can read long reads with single base pair resolution. The present disclosure also incorporates the addition of a translocating protein such as a biological polymerase as a method to bring DNA into the probing device described in U.S. patent application Ser. No. 16/009,766, filed on Jun. 15, 2018, and U.S. Provisional Application No. 62/581,366, filed on Nov. 3, 2017, which are both incorporated in their entirety by reference. The benefit of this modality is the translocating protein acts as a controlled localization site to bring the DNA into the sensing zone and at the same time provides a controlled rate of translocation within the sensing zone, which are two parameters to be control for single base resolution sequencing.

To achieve the goals of bringing a polynucleotide strand such as DNA down into the sensing zone, controlling the translocation speed, and reducing the number of fabrication steps required to produce a working device, a translocating protein such as DNA polymerase is bound to the surface on the dielectric gap or member between the oxidizing and reducing electrodes.

Figure 1A:
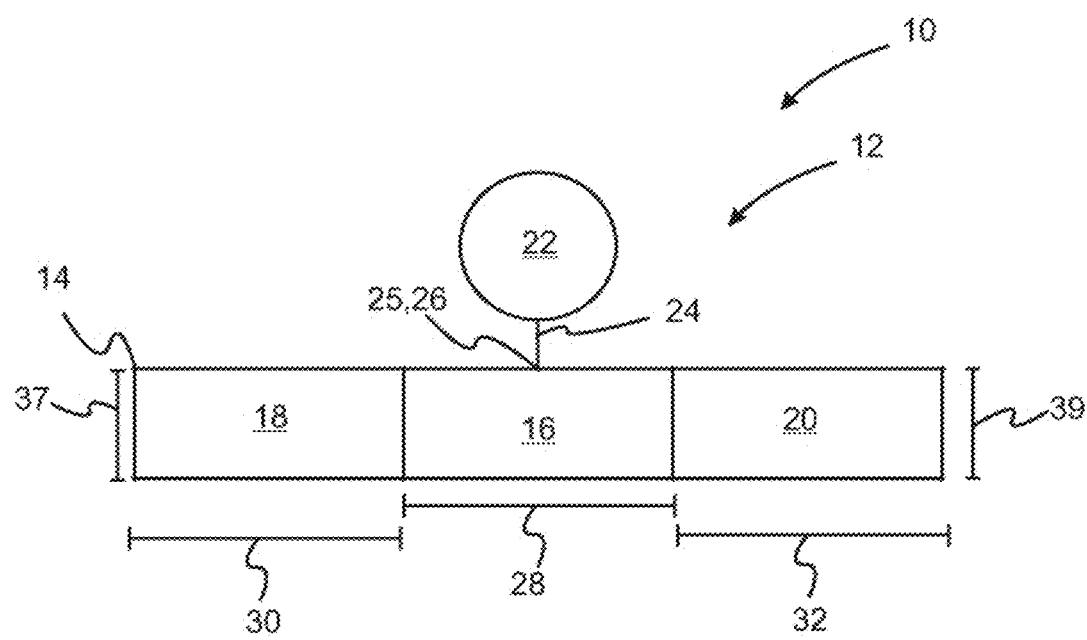
FIG. 1A shows a front view of a system for nucleic acid sequencing including a device.

FIG. 1A shows a system 10 for nucleic acid sequencing. The system 10 includes at least one device 12 that includes an oxidizing electrode 18, a reducing electrode 20, and a dielectric member 16 positioned between the oxidizing electrode 18 and reducing electrode 20. Characteristically, the dielectric member 16 separates the reducing electrode 20 from the oxidizing electrode 16 by a first distance 28 of at most 10 nm. A protein 22 is attached 24 to the surface 25 of the dielectric. The protein 22 is capable of translocating a polynucleotide strand having a nucleotide modified with a redox label or capable of receiving the modified nucleotide with a redox covalently bonded to the nucleoside base of the modified nucleotide. As is well known, nucleotides include nucleoside bases which are sometimes referred to as nucleobases. In this context, the term redox label includes completely functional redox labels or moieties that can react to form a functional redox label. Moreover the term "covalently bonded to the nucleoside base of the modified nucleotide" means that a moiety including the redox label is covalently bonded to the nucleotide. In at least one aspect, the modified nucleotide is modified because of the redox label bonded thereto. The attachment 24 of the protein 22 is such that the modified nucleotide with a redox label covalently bonded to the nucleoside base of the modified nucleotide of the polynucleotide strand passes to within a second distance that is at most 10 nm from the surface of the dielectric member during translocation. The oxidizing and reducing electrodes 18,20 generate an electric field that extends to a reaction area where the translocation of the polynucleotide strand through the protein occurs. Advantageously, the spatial dimensions allow a rapid electron transfer (i.e., nearly simultaneously) from the reducing electrode to redox label to the oxidizing electrode when the modified nucleotide with a redox label covalently bonded to the nucleoside base of the modified nucleotide is located at the reaction area. Mover, the spatial dimensions are such that diffusional is not an important contributor to electron transport.

FIG. 1A also shows the device 12 including an electrode pair format device 14 including a dielectric member 16 positioned between oxidizing biased electrode or oxidizing electrode 18 and a reducing biased electrode or reducing electrode 20. U.S. patent application Ser. No. 16/009,766 and U.S. Provisional Application No. 62/581,366 disclose example embodiments of the electrode pair format device 14 and methods of fabricating the electrode pair format device 14. U.S. patent application Ser. No. 16/009,766 and U.S. Provisional Application No. 62/581,366 both disclose methods of DNA sequencing using a redox label and a shuttling principle. Briefly, a shuttling detection mechanism involves two electrodes separated by a nanoscale thick dielectric. The electrodes are held at an oxidizing and a reducing potential to enable a reversible electrochemical reaction of a redox molecule. The small space between the two electrodes is called a sensing zone, which is small enough for a redox molecule to interact with both electrodes and complete the electrical circuit. While the redox molecule resides in the sensing zone, electrons can "shuttle" between reducing and oxidizing electrodes, producing an amplified current signal, which is much higher than a signal expected from a single electron transfer event. This mechanism is different from nanogap devices, where a redox molecule must diffuse back and forth between the electrodes in order to produce a measurable electrical signal.

The dielectric member 16 of various embodiments includes a material having a dielectric constant such that fluctuations in a tunnel current between the oxidizing electrode 18 and reducing electrode 20 are less than the changes in current flow result from the electron transfer from the reducing electrode 20, to redox label, and to oxidizing electrode 18. Examples of materials include hafnium and zirconium silicates, metal oxides or nitrides, such as aluminum oxide, titanium dioxide, hafnium oxide, zirconium oxide, silicon oxide, silicon nitride, and hexagonal boron nitride.

In various embodiments, the dielectric member 16 separates the reducing electrode 20 from the oxidizing electrode 18 by a first distance 28 of at most 10 nm. In various embodiments, the dielectric member 16 has a width 28 between the oxidizing electrode 18 and reducing electrode 20 ranging from 1 nm to 10 nm, preferably ranging from 1 nm to 4 nm. In various embodiments, the width 28 of the dielectric member 16 between the oxidizing electrode 18 and reducing electrode 20 is 0.5 nm, 1 nm, 1.25 nm, 1.5 nm, 1.75 nm, 2 nm, 2.25 nm, 2.5 nm, 2.75 nm, 3 nm, 3.2.5 nm, 3.5 nm, 3.75 nm, 4 nm, 4.25 nm, 4.5 nm, 4.75 nm, 5 nm, 5.25 nm, 5.5 nm, 5.75 nm, 6 nm, 6.25 nm, 6.5 nm, 6.75 nm, 7 nm, 7.25 nm, 7.5 nm, 7.75 nm, 8 nm, 8.25 nm, 8.5 nm, 8.75 nm, 9 nm, 9.25 nm, 9.5 nm, 9.75 nm, or 10 nm. In various embodiments, the width 28 of the dielectric member 16 is range between any two of the above specified widths.

One parameter is the cross-section arear of the dielectric member 16 defined by a thickness 35 and length 31, 33 between the oxidizing electrode 18 and reducing electrode 20. The cross-section area of the dielectric member 16 is preferably small enough to allow electron shuttling while providing sufficient insulation between the electrodes to avoid shorting.

Figure 1B:
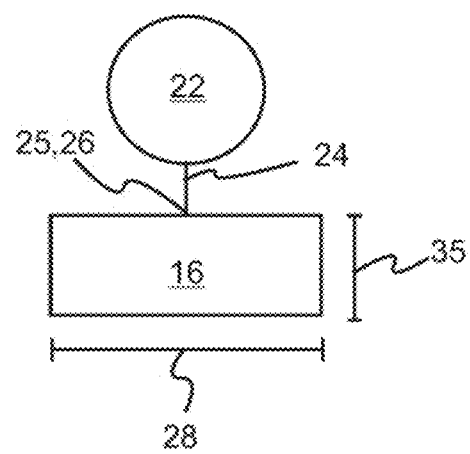
FIG. 1B show a front view of a translocating protein attached to a dielectric member.

In various embodiments as shown in FIG. 1B, the dielectric member 16 has a thickness 35 ranging from 5 nm to 5000 nm, preferably 10 nm to 1000 nm. In various embodiments, the thickness 35 of the dielectric member 16 is 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1500 nm, 2000 nm, 2500 nm, 3000 nm, 3500 nm, 4000 nm, 4500 nm, or 5000 nm. In various embodiments, the thickness 35 of the dielectric member 16 is range between any two of the above specified thicknesses.

In various embodiments, the oxidizing electrode 18 has a width 30 in contact with a sample or solution ranging from 5 nm to 5000 nm, preferably 10 nm to 1000 nm. In various embodiments, the width 30 of the oxidizing electrode 18 in contact with a sample or solution is 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1500 nm, 2000 nm, 2500 nm, 3000 nm, 3500 nm, 4000 nm, 4500 nm, or 5000 nm. In various embodiments, the width 30 of the oxidizing electrode 18 in contact with a sample or solution is range between any two of the above specified widths.

Figure 1C:
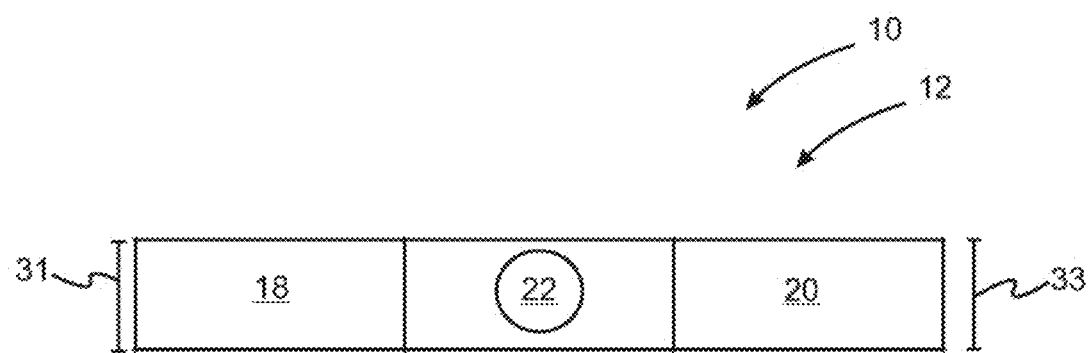
FIG. 1C shows a top view of a system for nucleic acid sequencing including a device.

In various embodiments has shown in FIG. 1C, the oxidizing electrode 18 has a length 31 in contact with a sample or solution ranging from 10 nm to 10000, preferably 50 nm to 5000 nm. In various embodiments, the length 31 of the oxidizing electrode 18 in contact with a sample or solution is 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1500 nm, 2000 nm, 2500 nm, 3000 nm, 3500 nm, 4000 nm, 4500 nm, 5000 nm, 6000 nm, 7000 nm, 8000 nm, 9000 nm, or 10000 nm. In various embodiments, the length 31 of the oxidizing electrode 18 in contact with a sample or solution is range between any two of the above specified lengths.

In various embodiments, the reducing electrode 20 has a width 32 in contact with a sample or solution ranging from 5 nm to 5000 nm, preferably 10 nm to 1000 nm. In various embodiments, the width 32 of the reducing electrode 20 in contact with a sample or solution is 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1500 nm, 2000 nm, 2500 nm, 3000 nm, 3500 nm, 4000 nm, 4500 nm, or 5000 nm. In various embodiments, the width 32 of the reducing electrode 20 in contact with a sample or solution is range between any two of the above specified widths.

In various embodiments has shown in FIG. 1C, the reducing electrode 20 has a length 33 in contact with a sample or solution ranging from 10 nm to 10000, preferably 50 nm to 5000 nm. In various embodiments, the length 33 of the reducing electrode 20 in contact with a sample or solution is 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1500 nm, 2000 nm, 2500 nm, 3000 nm, 3500 nm, 4000 nm, 4500 nm, 5000 nm, 6000 nm, 7000 nm, 8000 nm, 9000 nm, or 10000 nm. In various embodiments, the length 33 of the reducing electrode 20 in contact with a sample or solution is range between any two of the above specified lengths.

Figure 1D:
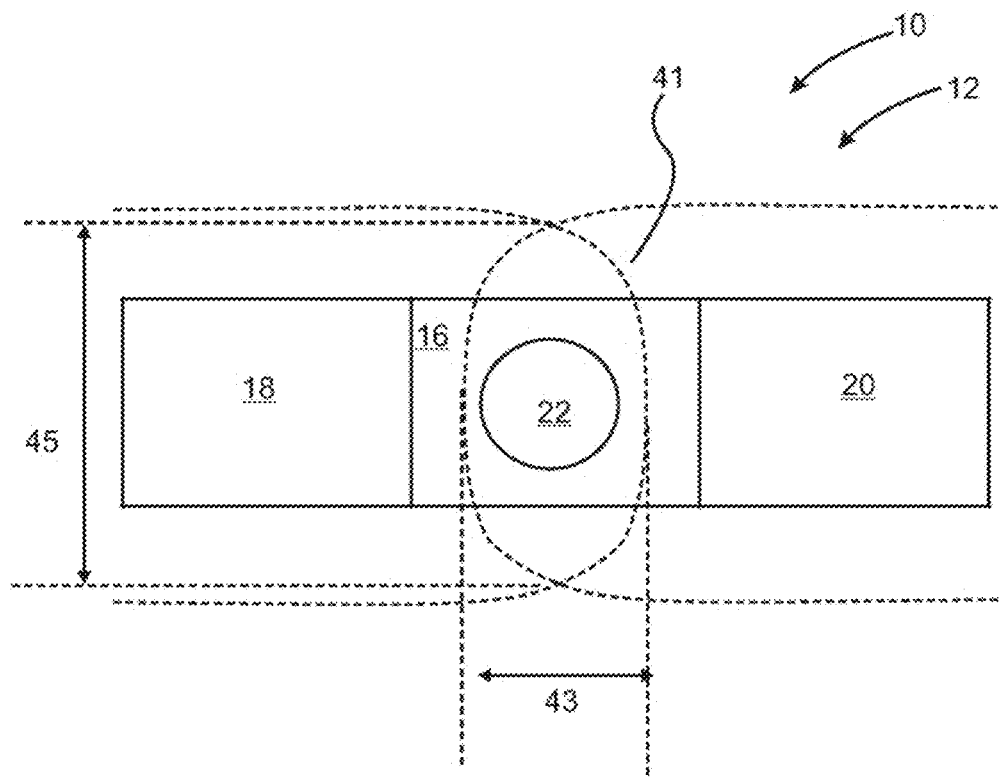
FIG. 1D shows a top view of a system for nucleic acid sequencing including an overlap from the reducing and oxidizing electrodes.
Figure 1E:
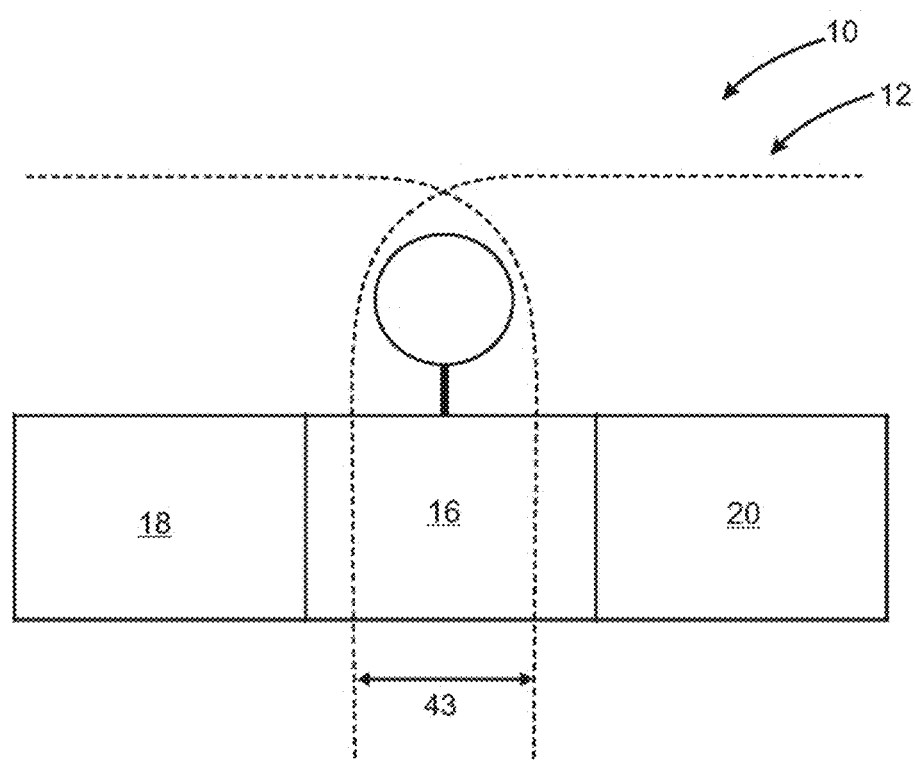
FIG. 1E shows a side view of a system for nucleic acid sequencing including an overlap from the reducing and oxidizing electrodes.

In various embodiments as shown in FIGS. 1D and 1E, the overlap 41 between the oxidizing electrode 18 and reducing electrode 20 has: a length 45 ranging 10 nm to 10000 nm, preferably 50 nm to 5000 nm; and a width 43 ranging from 1 nm to 10 nm, preferably 1 nm to 4 nm. The overlap 41 between the oxidizing electrode 18 and reducing electrode 20 can be understood to be the superposition of the electric fields from the oxidizing electrode 18 and reducing electrode 20.

The length 45 of the overlap 41 of various embodiments is 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1500 nm, 2000 nm, 2500 nm, 3000 nm, 3500 nm, 4000 nm, 4500 nm, 5000 nm, 6000 nm, 7000 nm, 8000 nm, 9000 nm, or 10000 nm. In various embodiments, the length 45 is range between any two of the above specified lengths.

The width 43 of the overlap 41 of various embodiments is width 28 of the dielectric member 16 between the oxidizing electrode 18 and reducing electrode 20 is 0.5 nm, 1 nm, 1.25 nm, 1.5 nm, 1.75 nm, 2 nm, 2.25 nm, 2.5 nm, 2.75 nm, 3 nm, 3.25 nm, 3.5 nm, 3.75 nm, 4 nm, 4.25 nm, 4.5 nm, 4.75 nm, 5 nm, 5.25 nm, 5.5 nm, 5.75 nm, 6 nm, 6.25 nm, 6.5 nm, 6.75 nm, 7 nm, 7.25 nm, 7.5 nm, 7.75 nm, 8 nm, 8.25 nm, 8.5 nm, 8.75 nm, 9 nm, 9.25 nm, 9.5 nm, 9.75 nm, or 10 nm. In various embodiments, the width 43 is range between any two of the above specified widths.

In various embodiments, the oxidizing electrode 18 or reducing electrode 20 is a planar electrode. The oxidizing electrode 18 or reducing electrode 20 of various embodiments includes materials such as titanium nitride, palladium, or platinum. Examples of electrodes for use in the systems and devices of various embodiments are disclosed in U.S. Patent Application Publication No. 2017/0370870 which is incorporated in its entirety by reference.

The translocating protein 22 is a protein capable of binding to a polynucleotide strand such as double-stranded or single-stranded DNA and RNA and translocate or shuttle the polynucleotide strand through the protein. Examples of translocating proteins include DNA polymerase such as Taq polymerase, RNA polymerase such as T7 RNA polymerase, ribosome, single-stranded binding protein, topoisomerase, helicase, nuclease, exonuclease, endonuclease, a zinc finger nuclease, an RNA guided DNA endonuclease, a transcription activator-like effector nuclease, and a CRISPR protein.

For example, other potential enzymes to hold and scan through a DNA strand include nucleases such as exonucleases, endonucleases, deoxyribonucleases, and ribonucleases; helicase enzymes, and CRISPR proteins. Examples of CRISPR proteins are CRISPR-Cas type and CRISPR-associated proteins, including but not limited to Cas9 and Csf1. In the case of CRISPR associated enzymes, the device of various embodiments includes using a gRNA target as a guide that would be designed to not recognize any part of the DNA strand being sequenced. The enzyme controls the translocation and readout of the whole target DNA within the sensing zone.

In various embodiments, the protein 22 is attached to a surface 25 of the dielectric member 16 such that the modified nucleotide with a redox label covalently bonded to the nucleoside base of the modified nucleotide of the polynucleotide strand passes at most 10 nm from the surface of the dielectric member. In various embodiments, the protein is attached to a surface of the dielectric member such that the modified nucleotide with a redox label covalently bonded to the nucleoside base of the modified nucleotide of the polynucleotide strand passes 0 nm, 0.25 nm 0.5 nm, 0.75 nm, 1 nm, 1.25 nm, 1.5 nm, 1.75 nm, 2 nm, 2.25 nm, 2.5 nm, 2.75 nm, 3 nm, 3.25 nm, 3.5 nm, 3.75 nm, 4 nm, 4.25 nm, 4.5 nm, 4.75 nm, 5 nm, 5.25 nm, 5.5 nm, 5.75 nm, 6 nm, 6.25 nm, 6.5 nm, 6.75 nm, 7 nm, 7.25 nm, 7.5 nm, 7.75 nm, 8 nm, 8.25 nm, 8.5 nm, 8.75 nm, 9 nm, 9.25 nm, 9.5 nm, 9.75 nm, or 10 nm from the surface of the dielectric member. In various embodiments, the distance that the modified nucleotide with a redox label covalently bonded to the nucleoside base of the modified nucleotide of the polynucleotide strand passes from the surface of the dielectric member is a range between any two of the above specified distances.

FIGS. 2A, 2B, 2C, 3, and 4 show the device 12 incorporated within different structures.

Figure 2A:
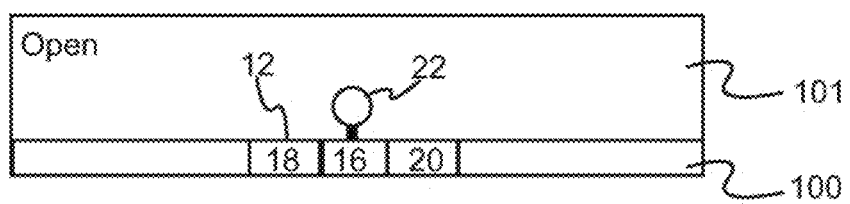
FIGS. 2A, 2B and 2C show schematics of three different geometries for modification of the planar electrode pair.
Figure 2B:
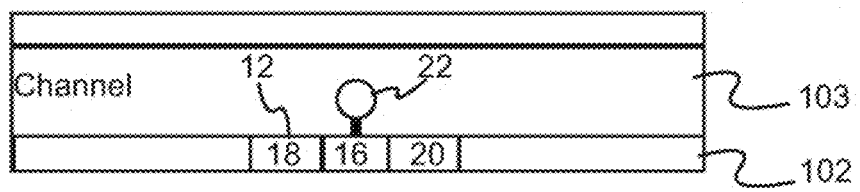

FIG. 2A shows the device 12 including electrodes 18,20 and dielectric member 16 with an attached translocating protein 22 in an arrangement 100 exposing the device 12 or protein 22 an opening 101 to which a sample can be added. FIG. 2B shows the device 12 including electrodes 18,20 and dielectric member 16 with an attached translocating protein 22 incorporated within a wall 102 of a channel (a nanochannel), where the device 12 or protein 22 is exposed to a channel 103 to which a sample can be added. A protein such as polymerase being attached on the dielectric member between the planar electrodes does not require a nanochannel but can be within a channel or open solution as illustrated in FIG. 14 (Open and Channel)

Figure 2C:
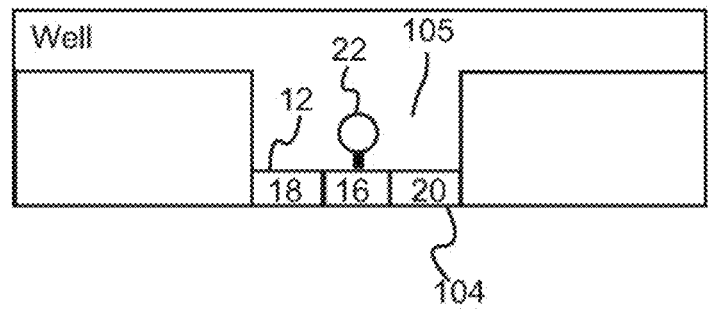

FIG. 2C shows the device 12 including electrodes 18,20 and dielectric member 16 with an attached translocating protein 22 as the floor 104 of a well 104. The device 12 or protein 22 is exposed to a channel 105 to which a sample can be added.

FIG. 3 shows a plurality of devices 12 as a part of a well 106. The devices 12 include electrodes 18,20 and dielectric member 16 with an attached translocating protein 22. As shown in FIG. 3, the well 106 has opposing side walls 108, 110 attached to a floor 112 that define a channel 114. A device 12 can be incorporated into the sidewalls 108, 110 or floor 112 such that the proteins 22 are positioned within the channel 114. For example, an alternate fabrication method is possible where the structure is formed at the edge of the well as illustrated in FIG. 3.

FIG. 4 shows side walls 116, 118 defining a channel 120 of a reduced size as compared to channel 114, where a device 12 can be incorporated into the side wall 116 such that the protein 22 is positioned within the channel 114. The devices 12 include electrodes 18,20 and dielectric member 16 with an attached translocating protein 22.

Methods of fabricating the electrode pair format device 14 of devices 12 shown in FIGS. 2A, 2B, 2C, 3, and 4 are described in U.S. patent application Ser. No. 16/009,766 and U.S. Provisional Application No. 62/581,366, with modifications.

Figure 5:
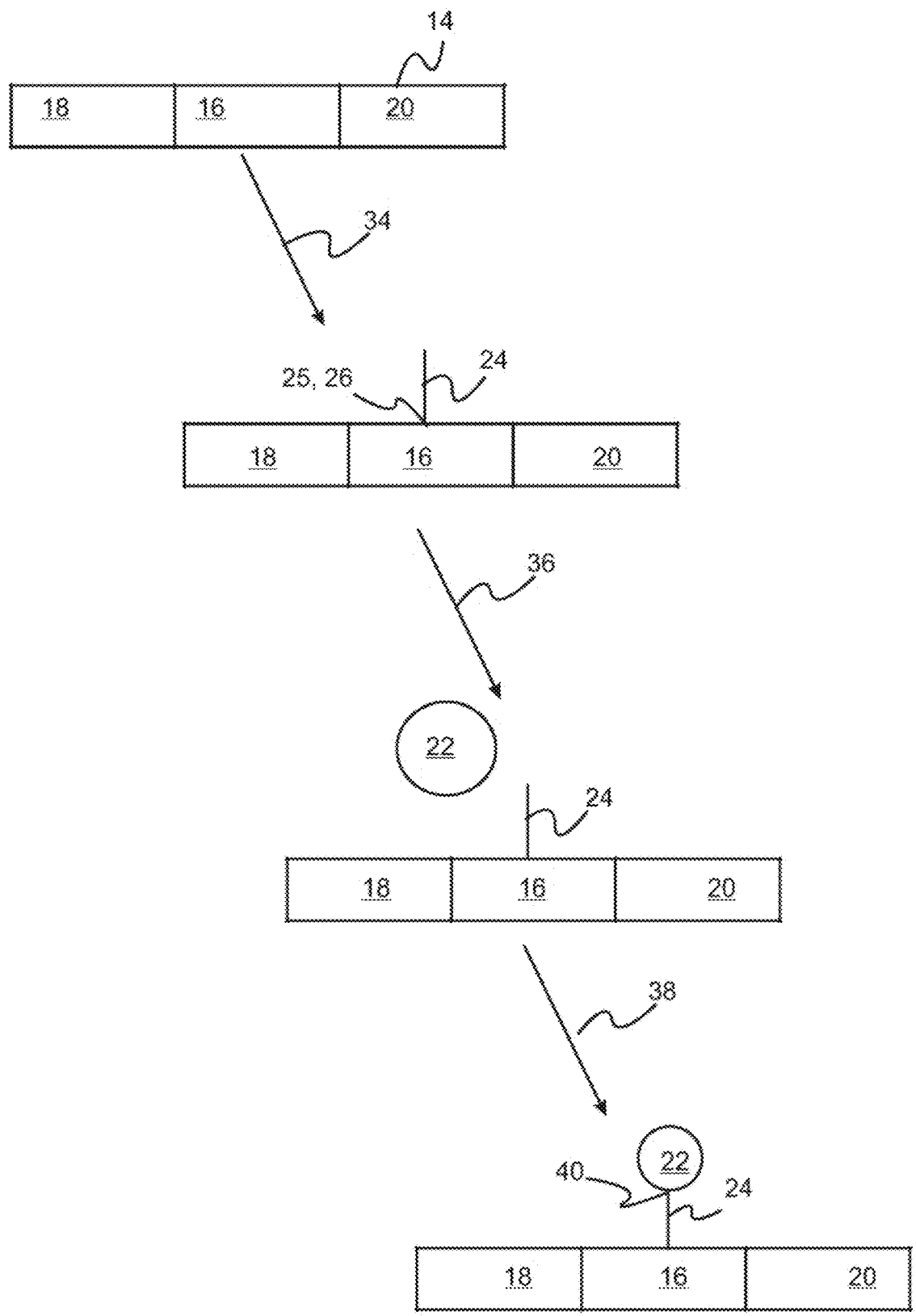
FIG. 5 shows a schematic of a process for fabricating the device.

FIG. 5 shows a schematic of a process of fabricating the device 12 of various embodiments. In step 34, the surface 25 of the dielectric member 16 is modified 26 to include an attaching agent 24. In steps 36 and 38, the translocating protein 22 is attached to the dielectric member 16 via attachment 40 to the attaching agent 24. The conjugation of the translocating protein 22 can be controlled by using bifunctional coupling agents 24 that react with the dielectric member on one end, for example silane chemistry or organophosphorous acids chemistry and biomolecules on the other, for example carboxyl, aldehyde, sulfonic, isothiocyanate, NHS ester, epoxide, or carbodiimide chemistry. It should be appreciated that steps 34, 36, and 38 (e.g., 34»36,38) can occurs sequentially, simultaneously, or in a different order (e.g., 36,38»34). The chemistry is preferably selective for the dielectric material (for example, Aluminum Oxide) vs metal electrodes, such that covalent binding occurs on the dielectric member between the electrodes and does not occur on top of the metal electrodes. In one example, the bifunctional coupling agent is 3-aminopropyltriethoxysilane. An example of attachment via silane chemistry is disclosed by Sin, Eun Jung, et al. "Surface modification of aluminum oxide for biosensing application." *Biomedical Engineering: Applications, Basis and Communications* 24.02 (2012): 111-116, which is incorporated in its entirety by reference. An example of attachment via organophosphorous acids chemistry is disclosed by Mutin, P. Hubert, et al, "Selective surface modification of SiO2- TiO2 supports with phosphonic acids." *Chemistry of materials* 16.26 (2004): 5670-5675, which is incorporated in its entirety by reference. Alternatively, the translocating protein can be physically adsorbed onto the dielectric layer, rather than covalently attached. In one example, the result is a polymerase that is covalently coupled between two electrodes where the binding pocket allows chemistry within to interact with the electrodes. As such when the DNA is being replicated when a redox modified base enters the enzyme active site it begins to undergo an electrochemical oxidation and reduction reaction with the electrodes. This allows electron shuttling that is used to detect the presence of the modified base that is used for sequencing.

Figure 6:
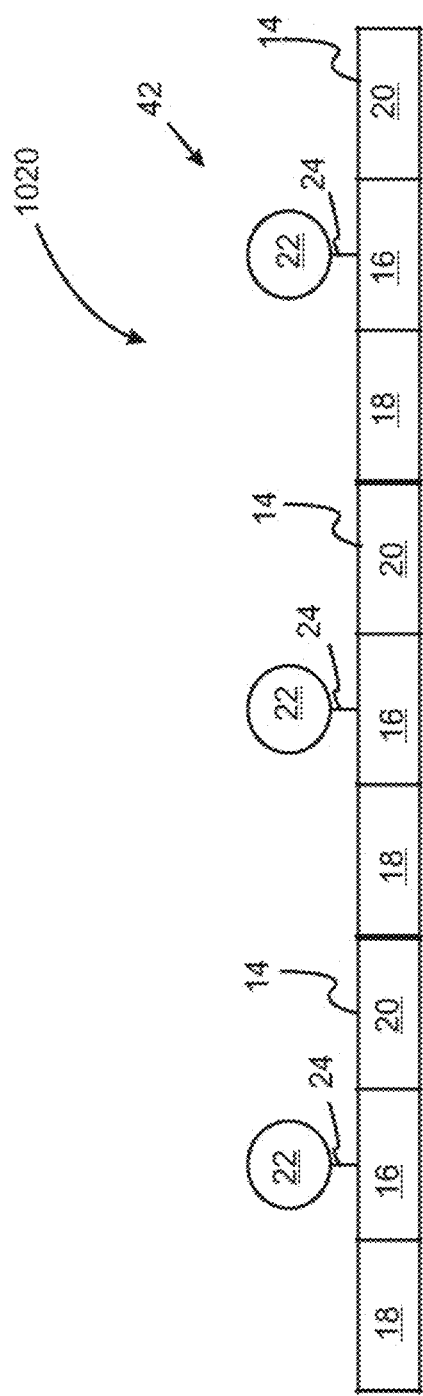
FIGS. 6 and 7 show systems including arrays of devices.
Figure 7:
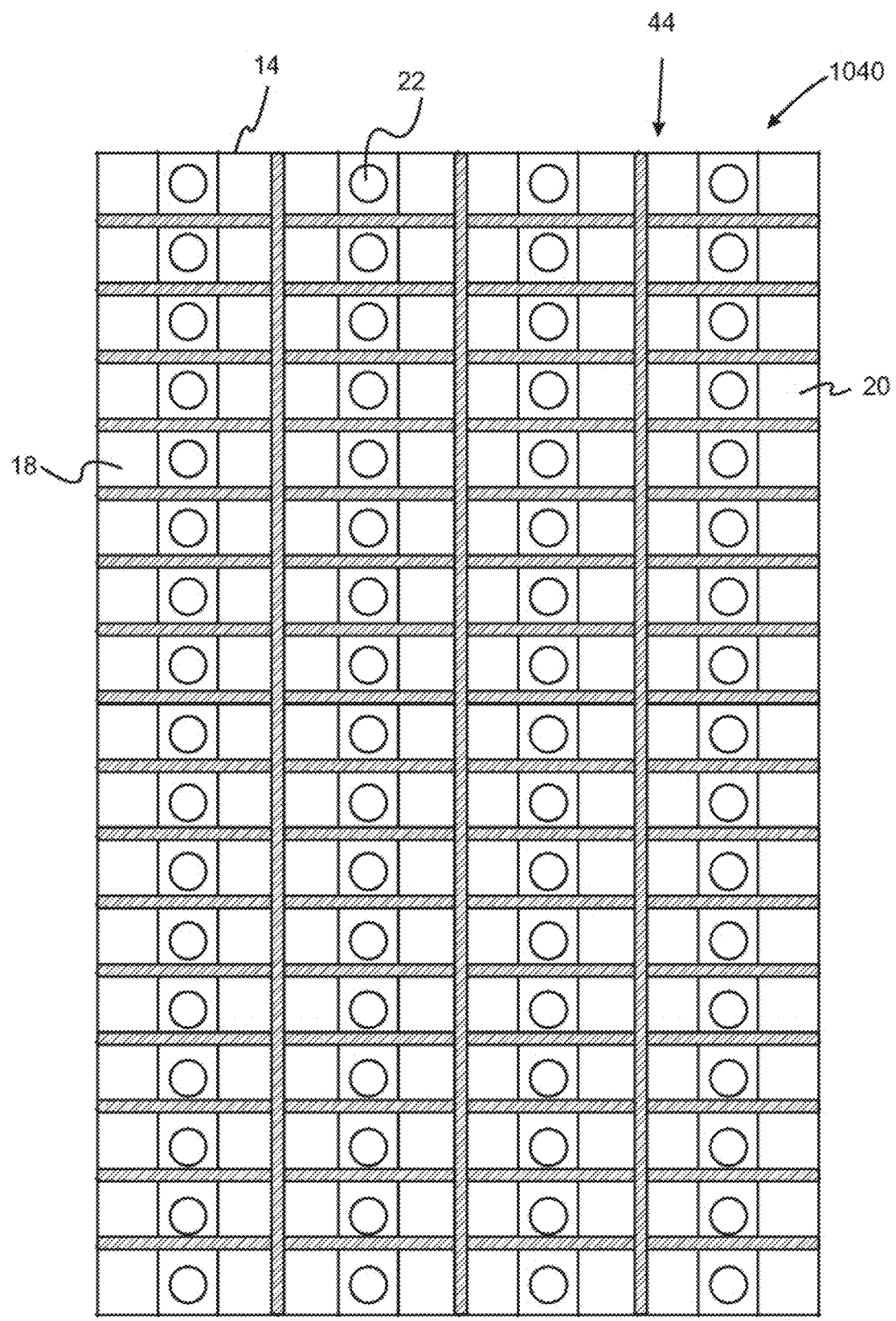

FIGS. 6 and 7 show systems 1020,1040 including arrays 42,44 of devices 12. In various embodiments, the systems include 1, 2, 3, 4, 5, 6, 7, 8, 9, 10, 25, 50, 75, 100, 250, 500, 750, 1000, 2500, 5000, 10000, or 100000 devices. In various embodiments, the number of devices is a range between any two of the above specified number devices. In a refinement, proteins in each of the arrays are uniformly distributed.

FIGS. 8A, 8B, 9A, and 9B show the proteins 22 are at least partially aligned on the surfaces of the dielectric members 16. In this regard, alignment means that the orientation of each protein's principle axes of inertia in a plurality of devices 12 is not random.

Figure 8A:
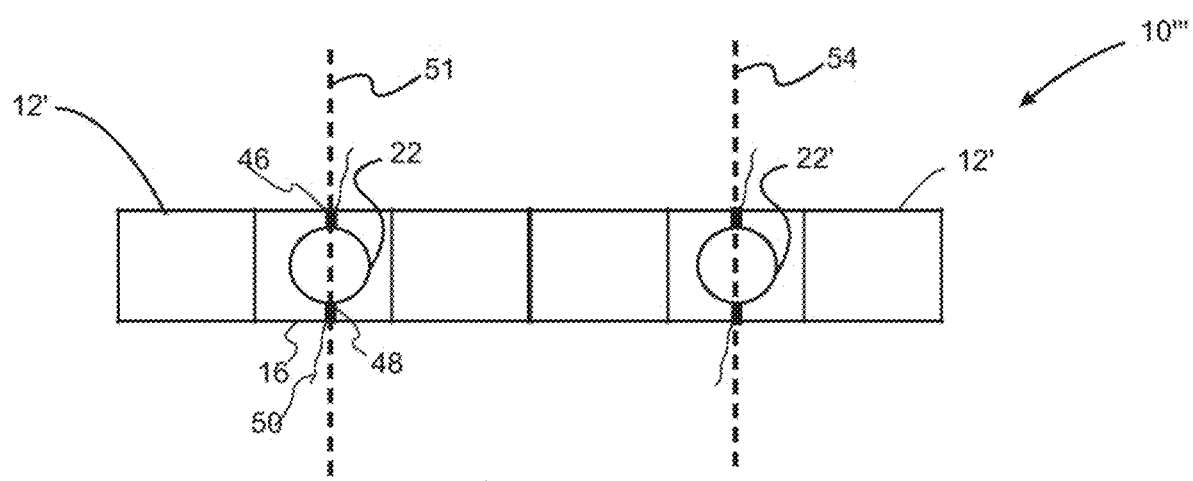
FIG. 8A shows a system including two devices.
Figure 8B:
FIG. 8B shows the principal axes of inertia for the proteins of the system of FIG. 8A.

FIG. 8A shows a system including two devices 12 with attached proteins 22, 22'. As shown in FIG. 8A, proteins 22 and 22' are aligned. In figure 8A, for simplicity, only corresponding principle axes of inertia 51 and 54 are depicted and shown to be aligned between the proteins. FIG. 8B shows the proteins 22 and 22' being oriented such that corresponding principal axes of inertia 51,54 can deviate from each other by angle $A_2$.

Figure 9A:
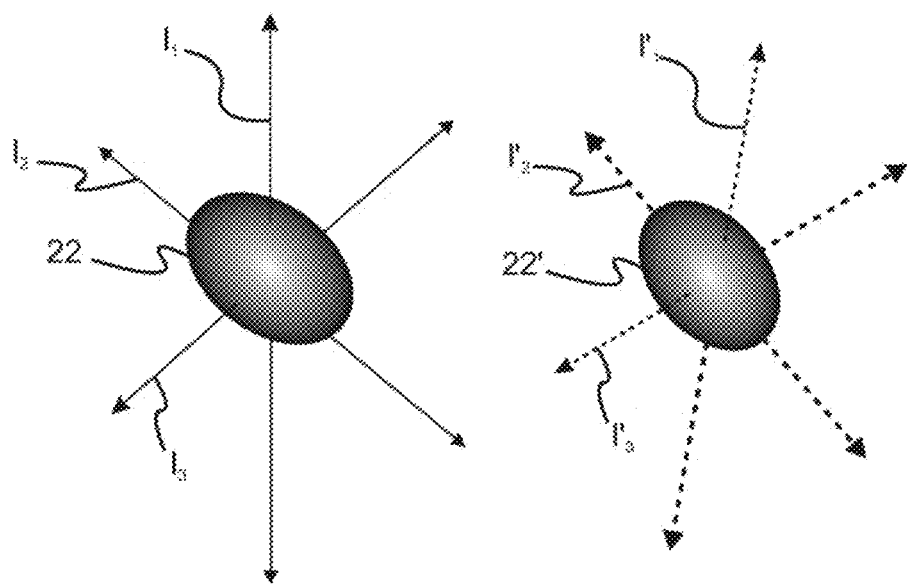
FIG. 9A shows a system including devices.
Figure 9B:
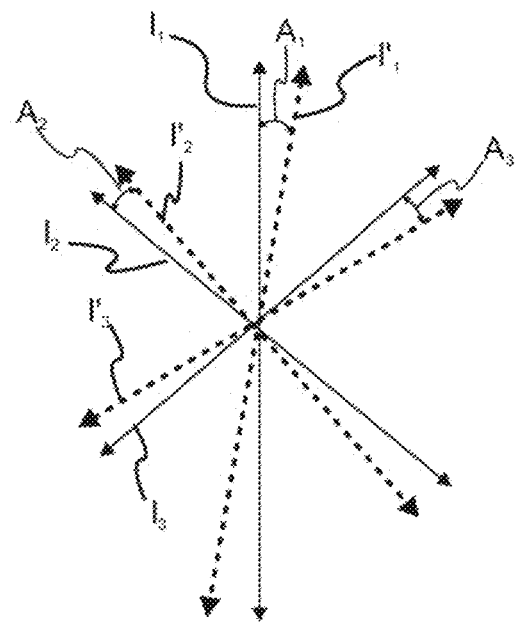
FIG. 9B shows the principal axes of inertia for the proteins of the system of FIG. 9A.

FIG. 9A and FIG. 9B show the general case where proteins 22 and 22' are slightly misaligned. Protein 22 defines associated principle axes of inertia $I_1, I_2, I_3$ while protein 22' defines associated principle axes of inertia $I'_1, I'_2, I'_3$. First principle axes of inertia $I_1, I'_1$ can deviate from each by at most angle $A_1$, second principal axes of inertia $I_2, I'_2$ can deviate from each other by at most angle $A_2$, and a third principal axes of inertia $I_3, I'_3$ can deviate from each other by at most angle $A_3$ where each of angles $A_1, A_2$, and $A_3$ are at most 60 degrees. Since proteins 22 are at least substantially uniformly oriented on the surfaces of the dielectric members 16, the deviation of corresponding principle axes of inertia among the proteins are with a relatively small angle of each other. In a refinement, $A_1, A_2$, and $A_3$ are at most 45 degrees. In a further refinement, $A_1, A_2$, and $A_3$ are at most 0°, 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, or 60°. In various embodiments, the deviation is a range between any two of the above specified degrees.

FIGS. 10 and 11 show the proteins 22 are at least partially aligned on the surfaces of the dielectric members 16. In this regard, alignment means the proteins are uniformly distributed over a predefined area which includes a plurality of devices 12.

FIG. 10 shows a system 1100 including three devices 12. As shown in FIG. 8, the proteins 22 are attached at positions such that the reaction areas where translocation 57 occurs within the protein 22 or sensing zones 57 for the oxidizing electrode 18 and reducing electrode 20 are at the same position relative to the dielectric member 16, FIG. 11 shows a system 1120 including three devices 12. As shown in FIG. 9, the proteins 22 are attached at different positions such that the reaction areas where translocation 57,57',57" occurs within the protein 22 or sensing zones 57,57',57" for the oxidizing electrode 18 and reducing electrode 20 are at within a zone 58. In various embodiments, the proteins are attached to the dielectric members such that the reaction areas or sensing zones of the proteins are at a distance that is 0 nm, 0.1 nm, 0.2 nm, 0.3 nm, 0.4 nm, 0.5 nm, 0.6 nm, 0.7 nm. 0.8 nm, 0.9 nm, 1 nm, 1.1 nm, 1.2 nm, 1.3 nm, 1.4 nm, 1.5 nm, 1.6 nm, 1.7 nm, 1.8 nm, 1.9 nm, and 2 nm of each other. In various embodiments, the distance is a range between any two of the above specified distances.

Figure 12:
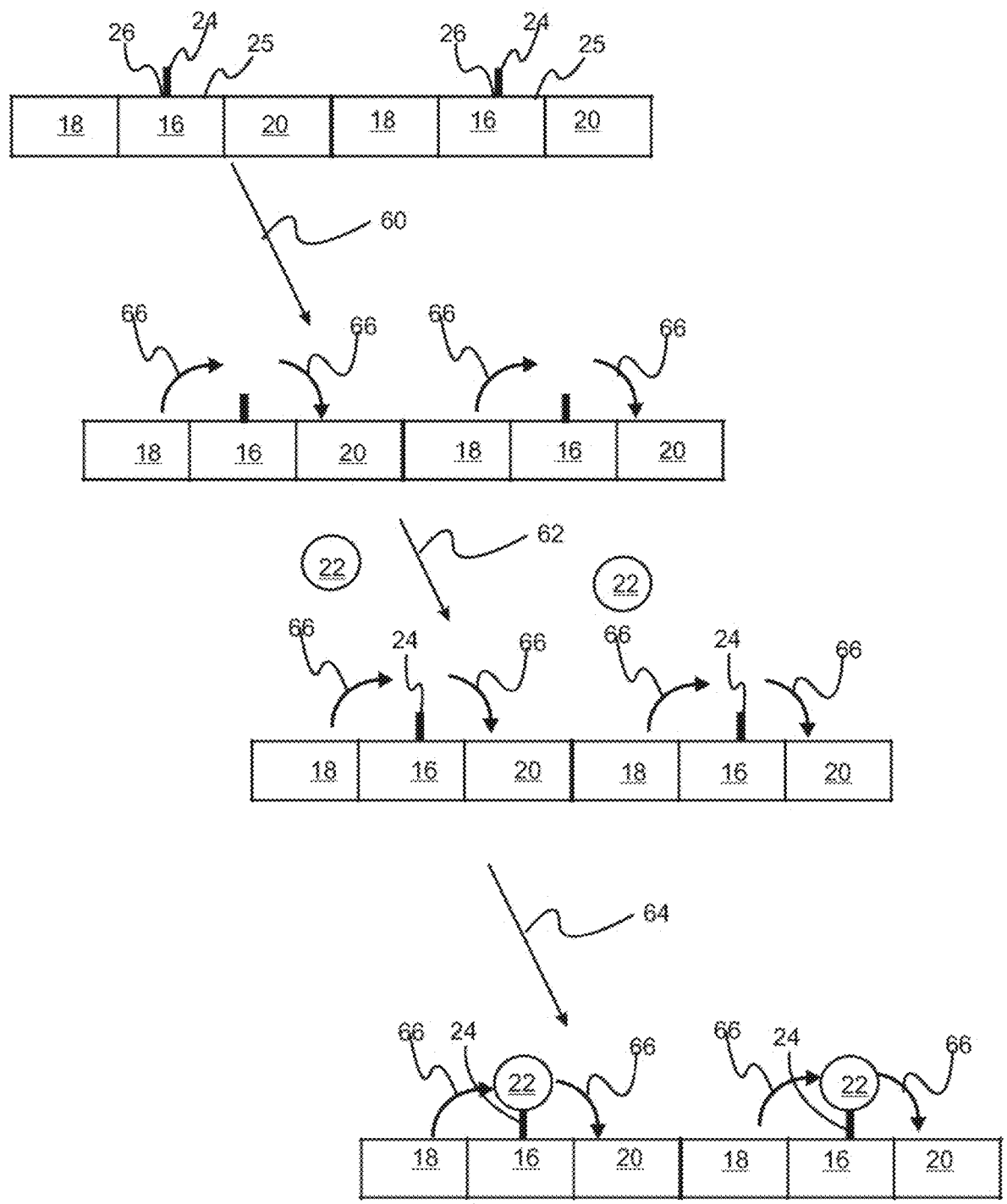
FIG. 12 shows a schematic of a process for fabricating the device.

FIG. 12 shows a schematic of fabricating of system 1020, 1040, 1100, 1120 including a method for forming nucleic acid sequencing devices. The method includes, prior to step 60, providing a device 14 including an oxidizing electrode 18, a reducing electrode 20, and a dielectric member 16. Characteristically, the dielectric member 16 separates the reducing electrode 20 from the oxidizing electrode 20 by a first distance of at most 10 nm. The method includes a second step 62 of generating an electric field 66 by the oxidizing electrode 18, the reducing electrode 16, or both. The method also includes a third step 64 of attaching 24 a protein 22 to a surface 25 of the dielectric member 16. The protein 22 is capable of translocating a polynucleotide strand having a nucleotide modified with a redox label or capable of receiving the modified nucleotide with a redox label covalently bonded to the nucleoside base of the modified nucleotide to a surface of the dielectric member such that the modified nucleotide with a redox label covalently bonded to the nucleoside base of the modified nucleotide of the polynucleotide strand passes by a second distance of at most 10 nm from the surface of the dielectric member during translocation. In step 64, the translocating proteins 22 such as polymerase are guided by the electrical field 66 to the dielectric members 16 and are induced by the electrical field 66 into a at least a substantially uniform orientation. In different examples, voltages can be chosen in a way that they attract electrically charged polymerases with symmetric forces so that the polymerase gets bound in between the electrodes. Alternatively, a lateral electric field can be created to control the orientation of the polymerase molecules such that a relatively uniform orientation can result in improved sensor performance. An example of lateral electric fields controlling orientations of proteins is disclosed in Emaminejad, Sam, et al, "Tunable control of antibody immobilization using electric field," *Proceeding of the National Academy of Sciences* 112.7 (2015): 1995-1999 which is incorporated in its entirety by reference.

For example, an electrical field generated by the electrodes during polymerase immobilization process can be used to guide the biomolecules to the dielectric layer and to induce a uniform orientation on the surface. For example, voltages can be chosen in a way that they attract electrically charged polymerases with symmetric forces so that the polymerase gets bound in between the electrodes. In the case when polymerase needs to be selectively adsorbed onto the dielectric layer, voltages on the electrodes can be set to create a surface charge unfavorable for polymerize attachment to the electrodes (adsorption is reduced when the surface charge matches the isoelectric point of polymerase). Alternatively, a lateral electric field can be created to control the orientation of the polymerase molecules, as uniform orientation can result in improved sensor performance (See Emaminejad et al.).

FIGS. 13, 14, 15, and 16 show methods for nucleic acid sequencing. The method includes a first step of providing at least one device including an oxidizing electrode 18, a reducing electrode 20, a dielectric member 16, and a protein 22 attached 24 to the surface 25 of the dielectric member 16. Characteristically, the dielectric member 16 separates the reducing electrode 20 from the oxidizing electrode 18 by a first distance of at most 10 nm. The protein 22 is capable of translocating a polynucleotide strand having a nucleotide modified with a redox label or capable of receiving the modified nucleotide with a redox label covalently bonded to the nucleoside base of the modified nucleotide. The attachment 64 of the protein 22 is such that the modified nucleotide with a redox label covalently bonded to the nucleoside base of the modified nucleotide of the polynucleotide strand passes to within a second distance that is at most 10 nm from the surface 25 of the dielectric member 16 during translocation. The method includes a third step of directing current through the oxidizing electrode 18 and reducing electrode 20, where the oxidizing electrode 18 and reducing electrode 20 generate an electric field that extends to a reaction area where the translocation of the polynucleotide strand through the protein 22 occurs. The method includes a third step of exposing the protein 22 to a sample including the polynucleotide strand that allows for the polynucleotide strand to be translocated through the protein 22. The method includes a fourth step of detecting changes in current flow in the oxidizing electrode 18 and reducing electrode 20. The changes identify electron transfer from the reducing electrode 20, to redox label, and to oxidizing electrode 18 when the modified nucleotide with a redox label covalently bonded to the nucleoside base of the modified nucleotide of the polynucleotide strand is at the reaction area.

FIG. 13 shows a device 12 including a dielectric member 16 between the oxidizing electrode 18 and the reducing electrode 20, where a DNA polymerase 22,68 is attached 24 to the dielectric member 16. An electrical field 66 is generated by the oxidizing electrode 18 and reducing electrode 20 when current is directed through the electrodes 18,20 are directed to a sensing zone 70 including an active site 72 of the DNA polymerase 68. Using a primer 74, the DNA polymerase 68 produces a complementary strand 76 to the base strand 78 by incorporating free deoxynucleotides (dNTPs) 80 and dNTPs modified 82 to include a redox label 83. As the modified dNTPs 82 or redox label enter the active site 72 and sensing zone 70 during DNA replication, electron transfer 84 occurs from the reducing, electrode 20, to redox label 83, and to oxidizing electrode 18. In embodiments as illustrated in FIG. 13, the redox label 83 would enter or be adjacent to the active site 72 during DNA replication by the polymerase 68, resulting in a base-specific signal every time a modified nucleotide with a redox label covalently bonded to the nucleoside base of the modified nucleotide 82 is incorporated. In a different example, the electron transfer can occur without diffusion of the redox label 83. As the speed of incorporation of the polymerase can be determined the bases can be assigned as a function of signal vs time. The device would operate such that one base is redox modified during the replication process at a time. Multiple devices can be run in parallel to achieve detection of different bases simultaneously. In the case of having redox species in solution, there is the chance that redox labeled species freely diffusing in solution would also interact within the electrodes. However, the time constant of a molecule freely diffusing through the sensing zone versus constrained in the sensing zone during incorporation would be different. Therefore, looking at the frequency domain of the signal would allow differentiation of a diffusion vs translocation signal. In different examples, the polymerase 68 is anchored to the surface of a nm scale dielectric member 16 between 2 electrodes 18,20. The polymerase 68 can bind with a DNA 78 and primer 74 and start incorporating nucleotides 80,82 via the polymerase chain reaction. The sensing zone 70 is within an overlap between the oxidizing electrode 18 and reducing electrode 20.

In various embodiments the electron transfer 84 from the reducing electrode 20, to redox label 83, and to oxidizing electrode 18 occurs at a rate (i.e. electron transfer rate) ranging from $\#\times 10^6$ s$^{-1}$ to $\#\times 10^{12}$ s$^{-1}$, where # is any value ranging from 1 to 10. In various embodiments, electron transfer rate is $\#\times 10^6$ s$^{-1}$, $\#\times 10^7$ s$^{-1}$, $\#\times 10^8$ s$^{-1}$, $\#\times 10^9$ s$^{-1}$, $\#\times 10^{10}$ s$^{-1}$, $\#\times 10^{11}$ s$^{-1}$, $\#\times 10^{12}$ s$^{-1}$, where # is any value ranging from 1 to 10. In various embodiments, the electron transfer rate is a rate selected between any two of the above specified rates. For example, the rate of electron transfer from the reducing electrode 20, to redox label 83, and to oxidizing electrode 18 occurs at a rate of $\#\times 10^6$ s$^{-1}$, where # is any value ranging from 1 to 10.

In various embodiments, the voltages of oxidizing 18 and reducing 20 electrodes in the directing step are different from each other.

In an alternative embodiment, the frontend of the electronics can be laid Out in a fully differential way. When current is flowing into one electrode of the frontend, a current with the same amplitude, but different polarity is flowing into the second input electrode of the frontend. This avoids disturbances that couple into both electrodes from being transmitted through the signal path. Examples of this embodiment are disclosed in are described in U.S. patent application Ser. No. 16/009,766 and U.S. Provisional Application No. 62/581,366.

In another embodiment, a high-pass characteristic is used in the very first stage of the frontend, which avoids differential DC currents (from tunneling or from currents flowing via the polymerase) that will overload the signal path of the frontend. This avoids that the signal from getting pushed to the limits of the measurement range due to "parasitic" DC currents. The change in current from the base for detection would be transmitted via the high-pass and processed in the electronic signal chain.

The redox label 83 of various embodiments is a compound capable of being oxidized by the oxidizing electrode 18 and reduced by the reducing electrode 20. Examples of redox labels include ferrocene (cyclopenta-1,3-diene;iron (2+)) and its derivatives, anthraquinone (anthracene-9,10-dione), methylene blue ([7-(dimethylamino)phenothiazin-3-ylidene]-dimethylazanium;chloride), and phenothiazine (10H-phenothiazine), osmium and ruthenium complexes, tetrathiafulvalene, aminophenol, nitrophenol, erythrosine B, ATTO MB2, etc. The redox species undergo reversible oxidation-reduction reaction under applied electrical potential in order to enable shuttling detection principle.

In various embodiments, the methods and systems include dNTPs 82 modified with different redox labels with each redox label having a different redox potential. In examples, the methods include two, three, or four nucleotides dNTPs having different redox labels. For example, adenine, thymine, or uracil may be modified to include a redox label and cytosine or guanine may be modified to include a different redox label. Examples of how a strand of DNA is replicated to incorporate redox-modified nucleotides is disclosed in U.S. patent application Ser. No. 16/009,766 and U.S. Provisional Application No. 62/581,366.

In various embodiments, the modified nucleotide with a redox label covalently bonded to the nucleoside base of the modified nucleotide 82 has the following formula:

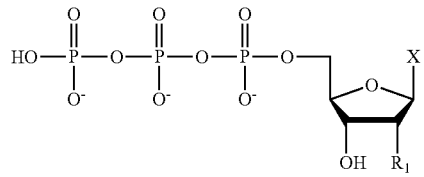

wherein:
X is

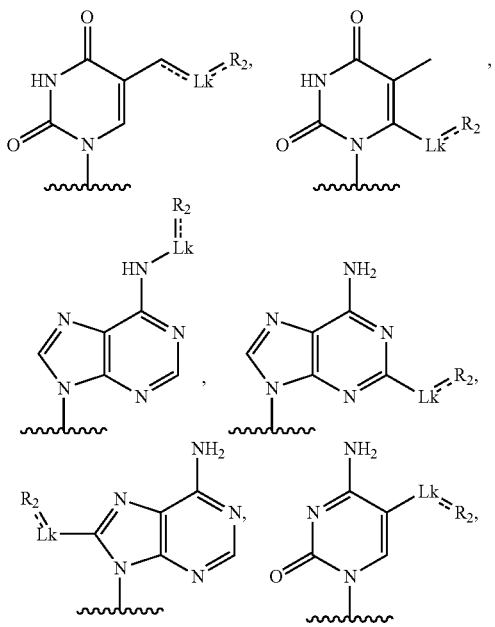
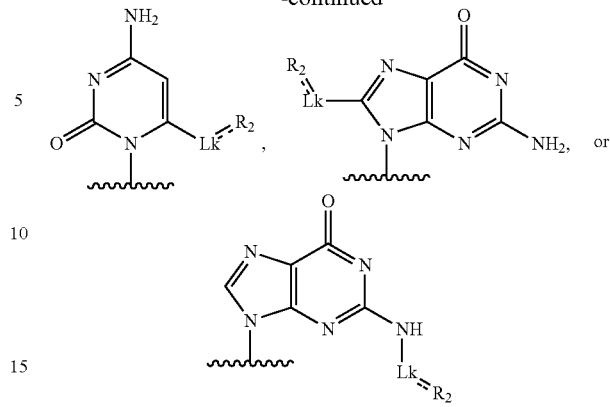

‍‍‍‍‍ is a single bond, a double bond, a triple bond,
Lk is absent or a hydrocarbon-containing linking group including, an alkyl, aryl, heteroalkyl, heteroaryl, cycloalkyl, or heteroatom-containing ring system,
$R_1$ is H or OH, and
$R_2$ is a redox label.

Examples of modified nucleotide with a redox label covalently bonded to the nucleoside base of the modified nucleotides 82 include compounds having the following formulas:

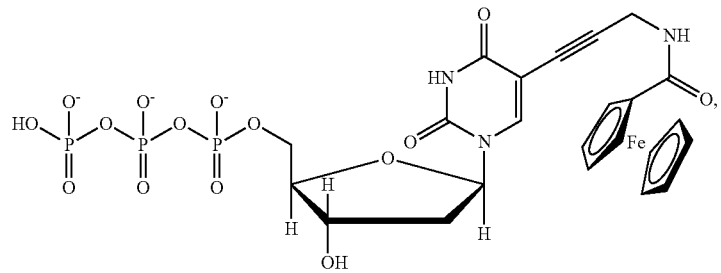

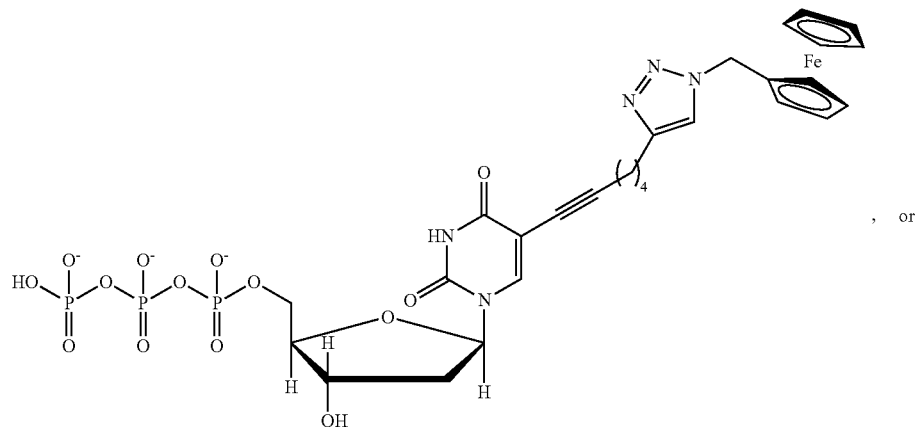

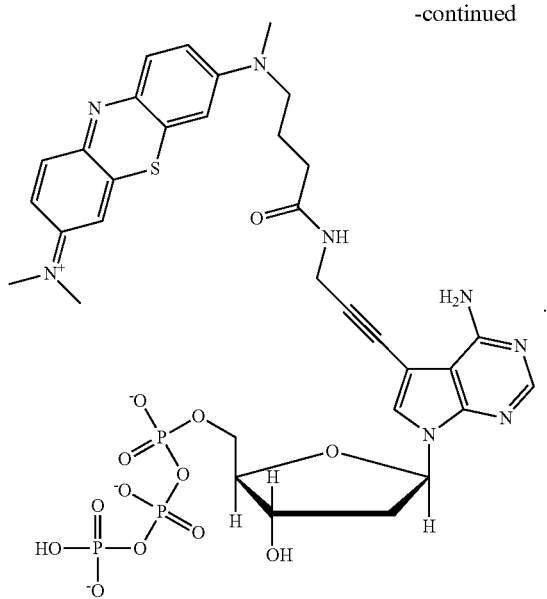
Examples of modified nucleotide with a precursor for a redox label covalently bonded to the nucleoside base of the modified nucleotides 82 include compounds having the following formulas:
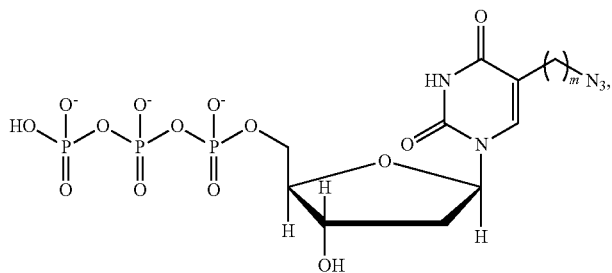
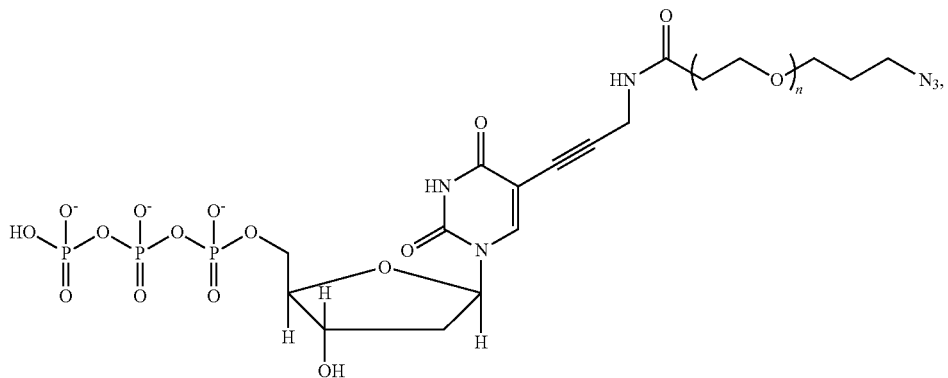

-continued
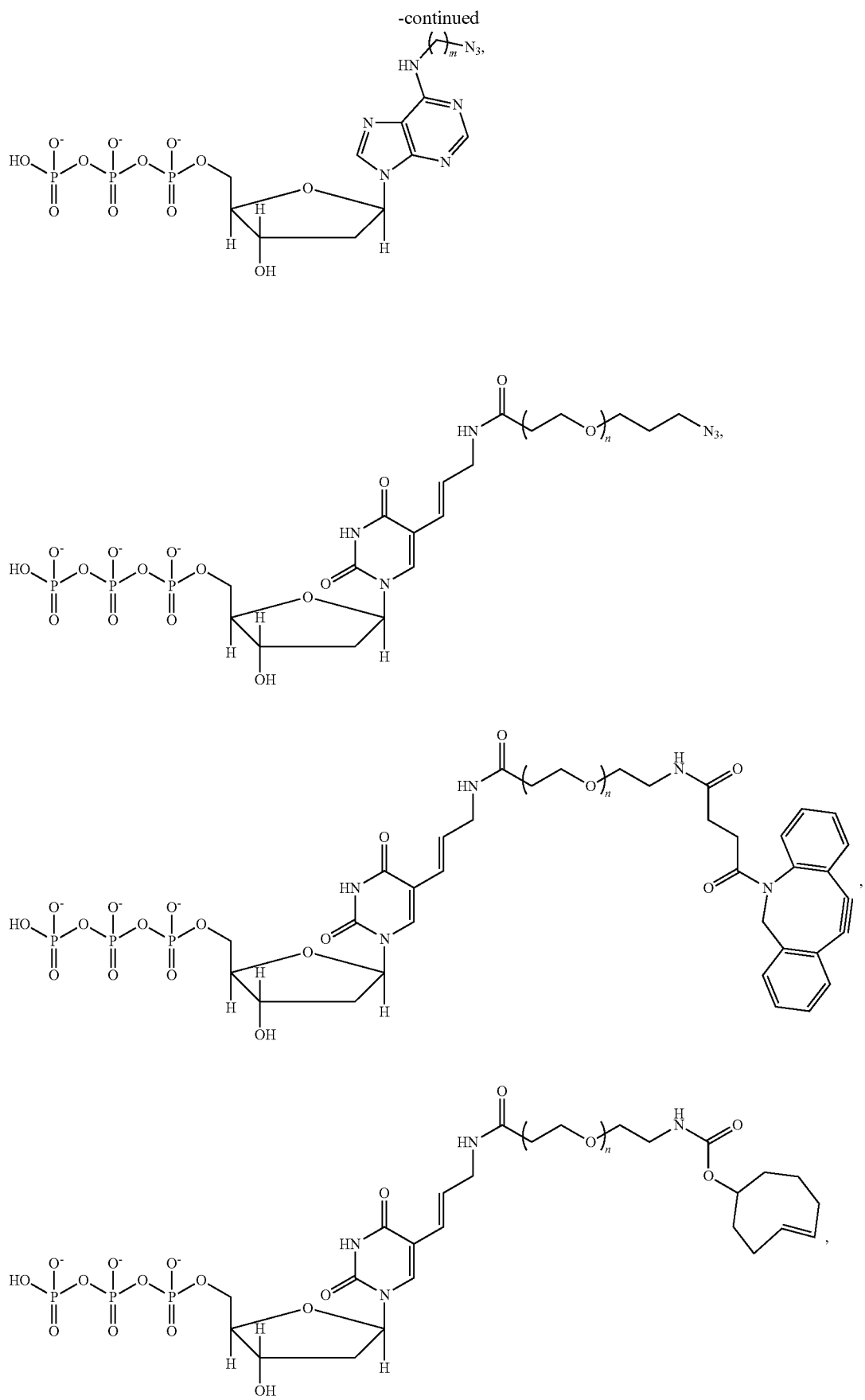

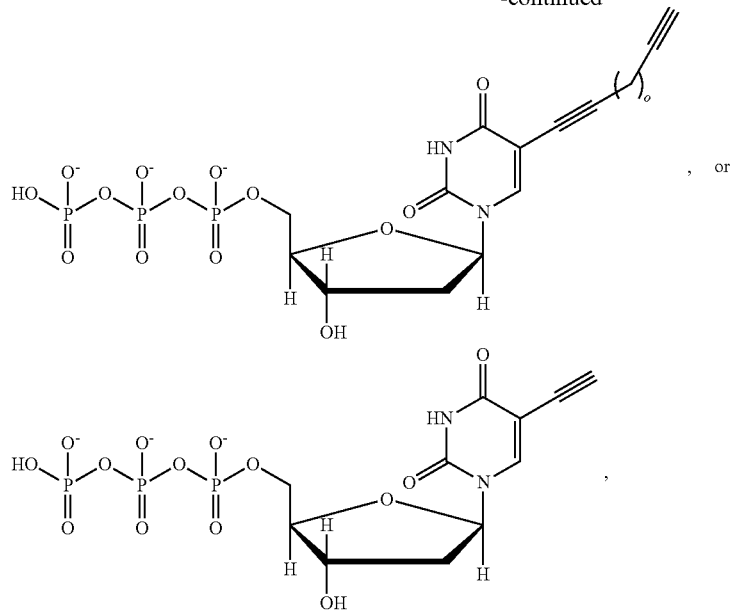

m is 1-12,
n is 1-100, and
is 3-12.

FIG. 14 is similar to FIG. 13 but differs in that the base strand 78' includes redox modified nucleotides 86 with redox labels attached thereto. Using a primer 74, the DNA polymerase 22,68 produces a complementary strand 76' to the base strand 78' by incorporating free dNTPs 80. As the modified nucleotides 86 or redox label 83 of the base strand 78' enters the active site 70 or sensing zone 72 during DNA replication, electron transfer occurs 84 from the reducing electrode 20, to redox label 83, and to oxidizing electrode 18 that changes current flow through the electrodes 18,20 and results in a base-specific signal. The method of incorporation can include either the DNA already having a single strand modified with a redox-incorporated species as illustrated in FIG. 14 is described in U.S. patent application Ser. No. 16/009,766 and U.S. Provisional Application No. 62/581,366. Alternatively, non-modified DNA is used and the redox-modified base is in solution.

FIG. 15 is similar to FIGS. 13 and 14 but differs in using a nuclease 22, 88 that is attached 24 to the dielectric member 16 instead of a DNA polymerase 68. The nuclease 88 binds to a polynucleotide strand 90 having redox modified nucleotides 86 with redox labels attached thereto. During digestion of the polynucleotide strand 90 into fragments 92, the nuclease 88 translocates the polynucleotide strand 90 such that the redox modified nucleotides 86 or redox label 83 of the polynucleotide strand 90 enters the sensing zone 70. Electron transfer then occurs 84 from the reducing electrode 20, to redox label 83, and to oxidizing electrode 18 that changes current flow through the electrodes 18,20 and results in a base-specific signal.

FIG. 16 is similar to FIGS. 13, 14, and 15 but differs in using a CRISPR-associated protein-9 nuclease 22,94 attached 24 to the dielectric member 16. A CRISPR single guide RNA (sgRNA) or CRISPR targeting RNA (crRNA) including a constant region 96 and a targeting region 98 is positioned within the CRISPR-associated protein-9 nuclease 94. The polynucleotide sequence of the targeting region 98 has a sequence such that. CRISPR-associated protein-9 nuclease 94 translocates the polynucleotide strand 90 having redox modified nucleotides 86,83 without creating a double strand break. During translocation, the modified nucleotides 86 or redox label 83 of the polynucleotide strand 90 enters the sensing zone 70. Electron transfer then occurs 84 from the reducing electrode 20, to redox label 83, and to oxidizing electrode 18 that changes current flow through the electrodes 18,20 and results in a base-specific signal.

In various embodiments, the electron transfer 84 from the reducing electrode 20, to redox label 83, and to oxidizing electrode 18 occurs at a rate (i.e. electron transfer rate) ranging from $\#10^6$ $s^{-1}$ to $\#\times10^{12}$ $s^{-1}$, where i is any value ranging from 1 to 10. In various embodiments, electron transfer rate is $\#\times10^6$ $s^{-1}$, $\#\times10^7$ $s^{-1}$, $\#\times10^8$ $s^{-1}$, $\#\times10^9$ $s^{-1}$, $\#\times10^{11}$ $s^{-1}$, $\#\times10^{12}$ $s^{-1}$, where # is any value ranging from 1 to 10. In various embodiments, the electron transfer rate is a rate selected between any two of the above specified rates. For example, the rate of electron transfer from the reducing electrode 20, to redox label 83, and to oxidizing electrode 18 occurs at a rate of $\#\times10^6$ $s^{-1}$, where # is any value ranging from 1 to 10.

In various embodiments, the voltages of oxidizing electrode 18 and reducing electrode 20 in the directing step are different from each other.

The redox label 83 of various embodiments is a compound capable of being oxidized by the oxidizing electrode and reduced by the reducing electrode. Examples of redox labels include ferrocene (cyclopenta-1,3-diene;iron(2+)) and its derivatives, anthraquinone (anthracene-9,10-dione), methylene blue ([7-(dimethylamino)phenothiazin-3-ylidene]-dimethylazanium;chloride), and phenothiazine (10H-phenothiazine), osmium and ruthenium complexes, tetrathiafulvalene, aminophenol, nitrophenol, erythrosine B, ATTO MB2, etc. The redox species undergo reversible oxidation-reduction reaction under applied electrical potential in order to enable shuttling detection principle.

In various embodiments, the methods and systems include nucleotides 86 modified with different redox labels each having a different potential. In examples, the methods include two, three, or four nucleotides having different redox labels. For example, adenine, thymine, or uracil may be modified to include a redox label and cytosine or guanine may be modified to include a different redox label. Examples of how a strand of DNA is replicated to incorporate redox-modified nucleotides is disclosed in U.S. patent application Ser. No. 16/009766 and FIGS. 4 and 5 and paragraphs [0017]-[0019] of U.S. Provisional Application No. 62/581,366.

In various embodiments, the modified nucleotide 86 has the following formula:

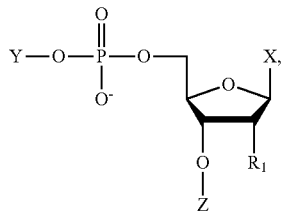

wherein:
Y is a ribose, deoxyribose, or hydrogen (H),
Z is a phosphate or hydrogen,
X is

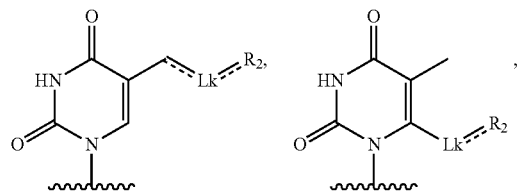

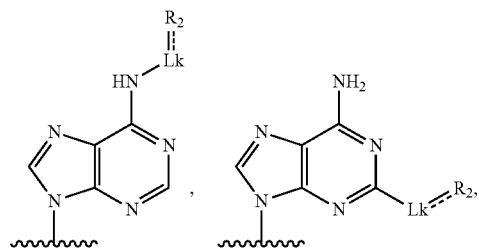

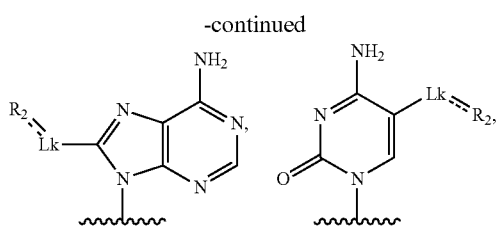

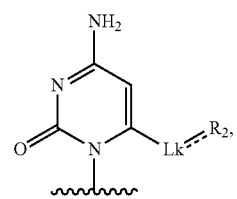

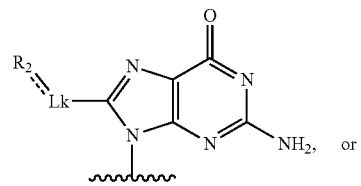, or

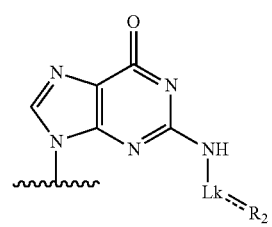

====== is a single bond, a double bond, a triple bond,
Lk is absent or a hydrocarbon-containing linking group including an alkyl, aryl, heteroalkyl, heteroaryl, cycloalkyl, or heteroatom-containing ring system,
$R_1$ is H or OH, and
$R_2$ is a redox label.

Examples of modified nucleotides 86 with redox labels attached thereto include compounds having the following formulas:

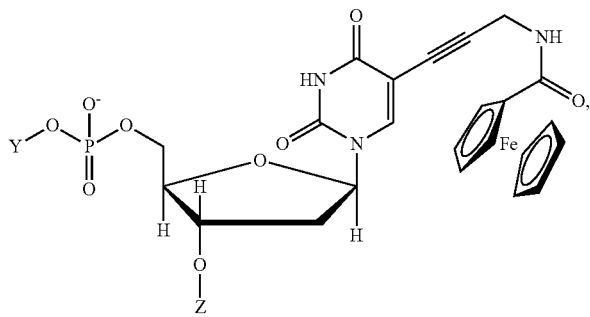

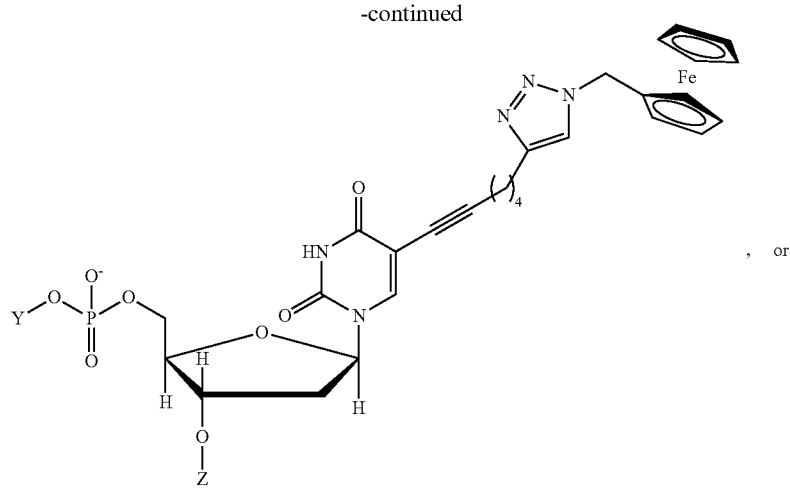
, or
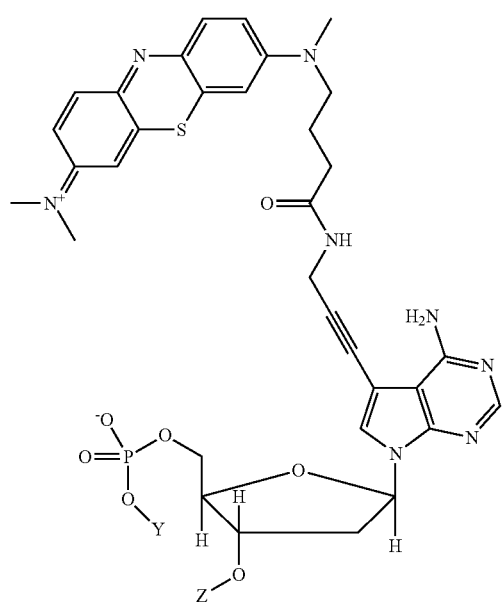
Examples of modified nucleotides 86 with redox label precursors attached thereto include compounds having the following formulas:
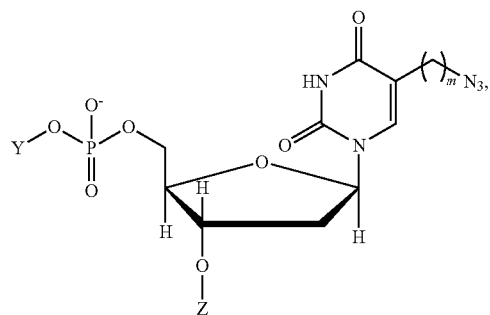

-continued
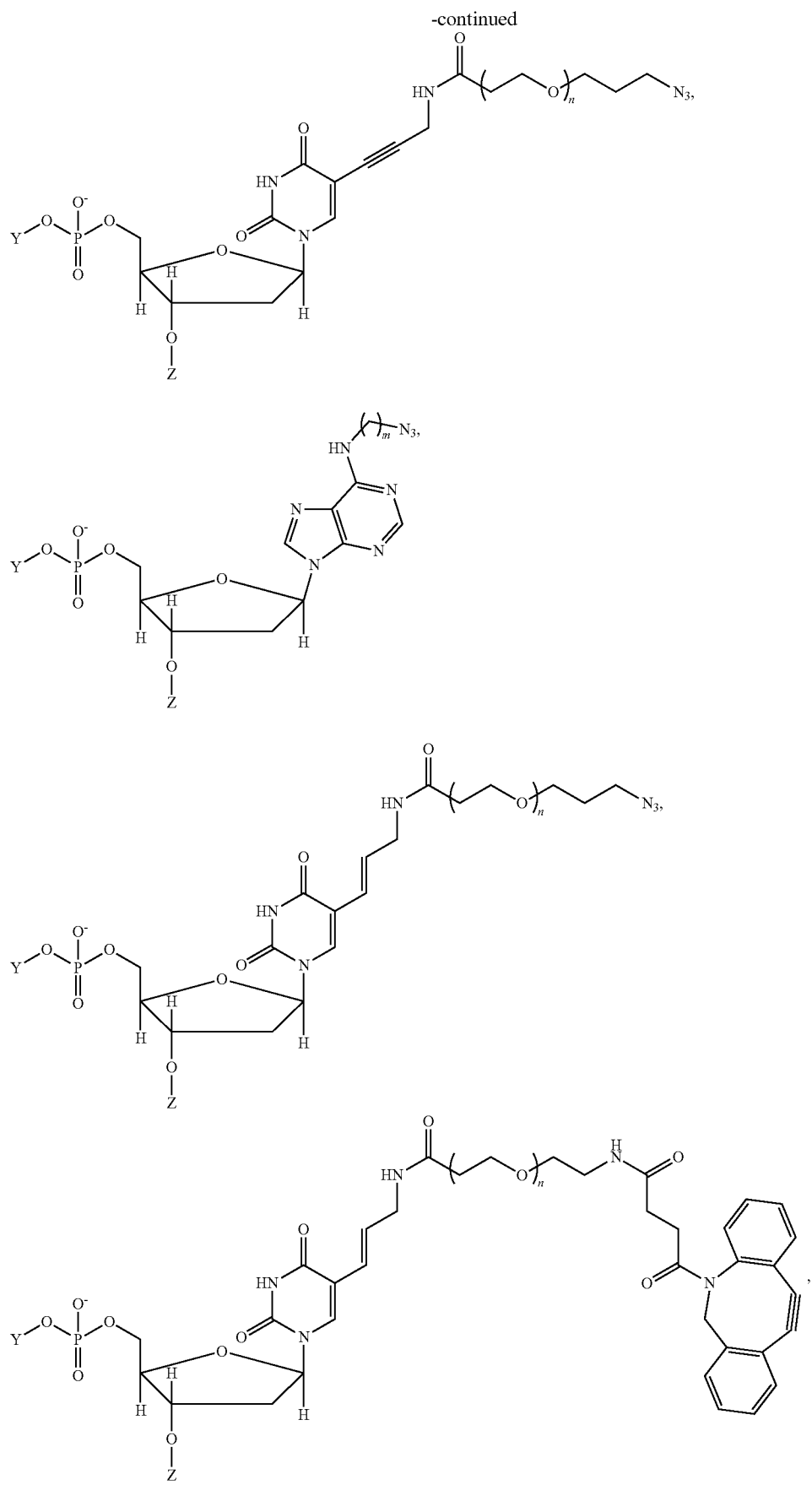

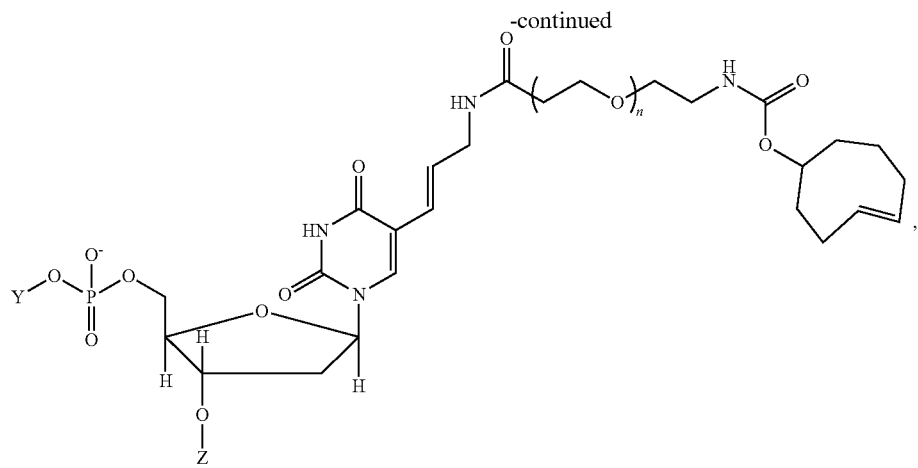

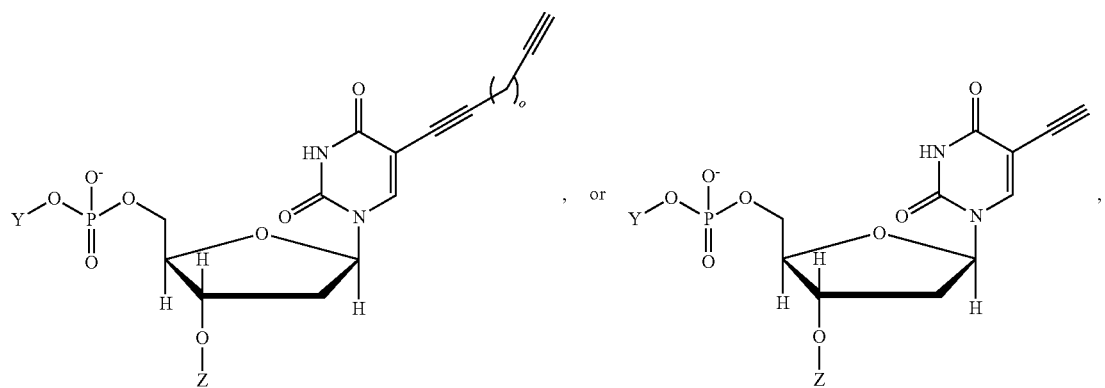

wherein
Y is a ribose, deoxyribose, or hydrogen (H),
Z is a phosphate or hydrogen,
m is 1-12,
n is 1-100, and
is 3-12.

Examples of methods of synthesizing modified dNTPs 82 or dNTPs forming the redox modified nucleotides 86 with redox labels attached thereto are provided below.

The redox label can be introduced into target DNA directly by synthesizing a nucleotide containing the label, which can be incorporated into the DNA strand during PCR. (FIGS. 17 and 18). Alternatively, a two-step approach can be used (FIG. 19): a nucleotide containing a chemical "handle" can be introduced into the DNA strand via PCR followed by another chemical modification step during which the electrochemical label attaches to the "handle". For this strategy, the main requirements are that the chosen chemical reaction is orthogonal to any other reactive groups present in the DNA molecule, compatible with aqueous solution, and quantitative. "Click" chemistry satisfies all of the above requirements and that has become a universal tool for modification of DNA and proteins, Click Chemistry is a reaction between azide and alkyne yielding covalent product—1,5-disubstituted 1,2,3-triazole, which is usually catalyzed by copper (I). For copper-free "click" reaction, sterically strained alkynes can be reacted with azides, or trans-cyclooctene can be coupled with tetrazine ("Third generation click chemistry"). Either the alkyne, trans-cyclooctene, azide or tetrazine handle can be introduced into the DNA via PCIS step in which a corresponding modified nucleotide (see Compounds 1-8) is introduced, followed by click reaction with an electrochemical label containing the other corresponding reactive group. The reactive group can be linked to the redox label through a carbon chain or ethylene oxide (PEG) chain (Compounds 9-12).

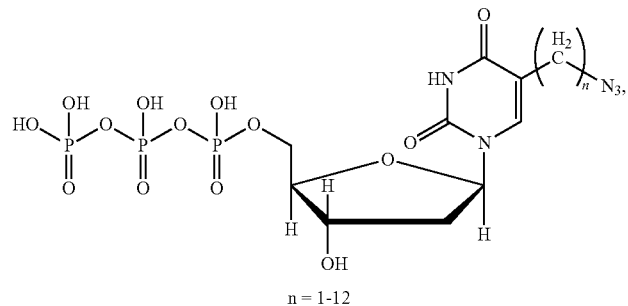
n = 1-12
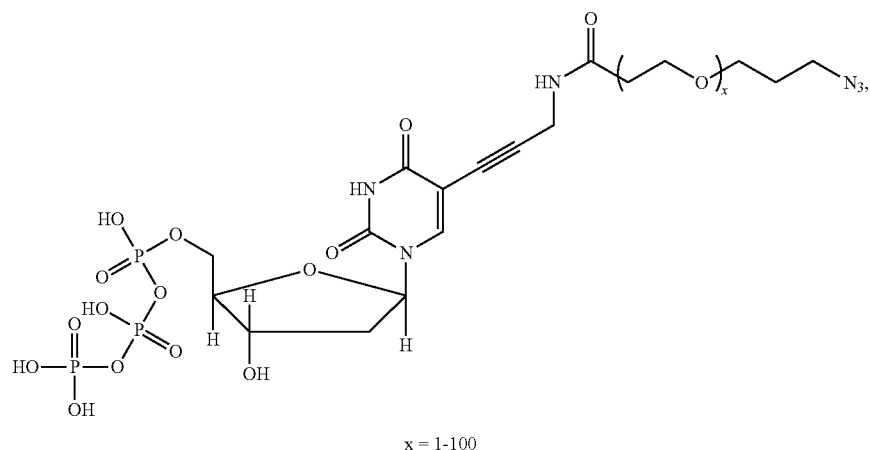
x = 1-100
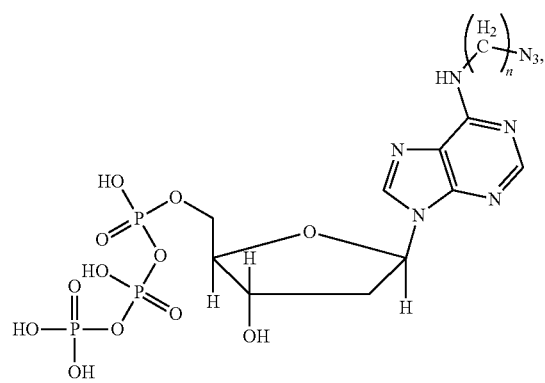
n = 1-12

-continued
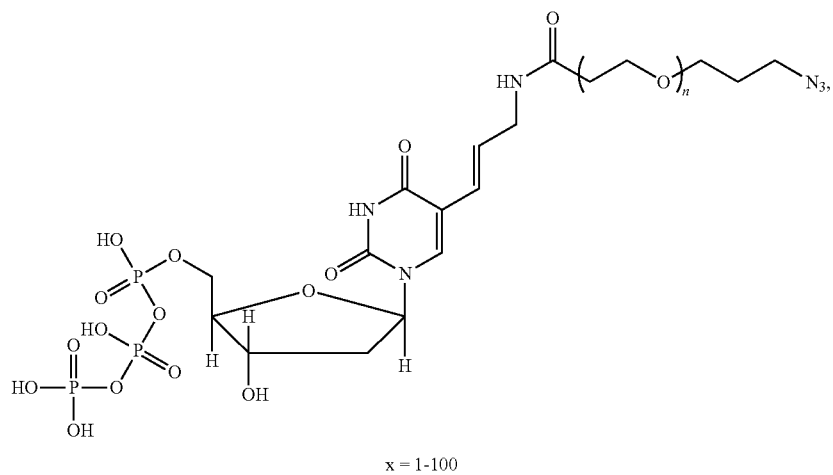
x = 1-100
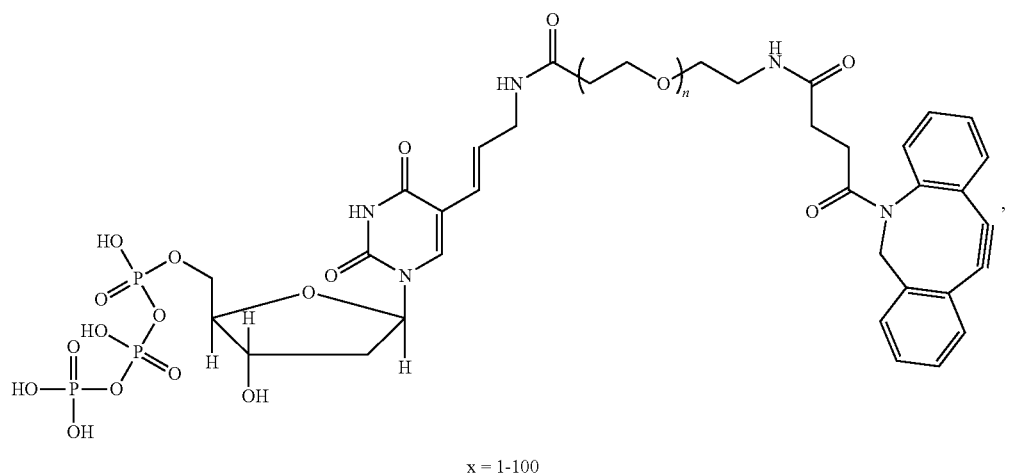
x = 1-100
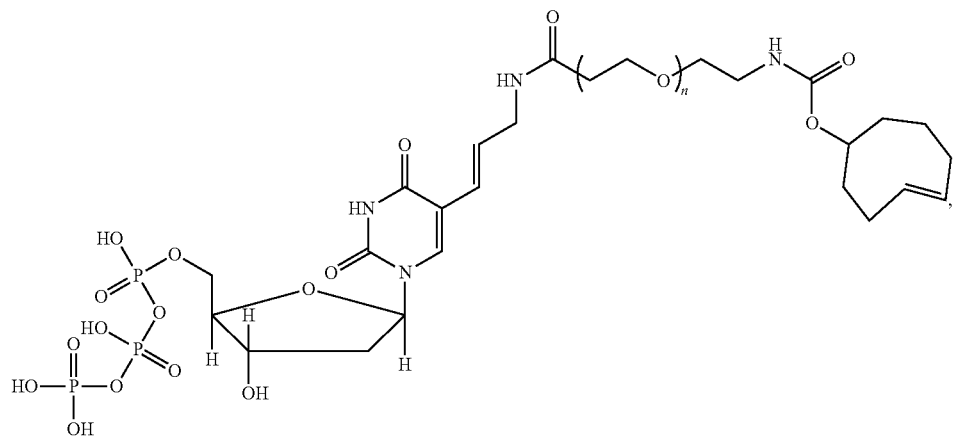
x = 1-100

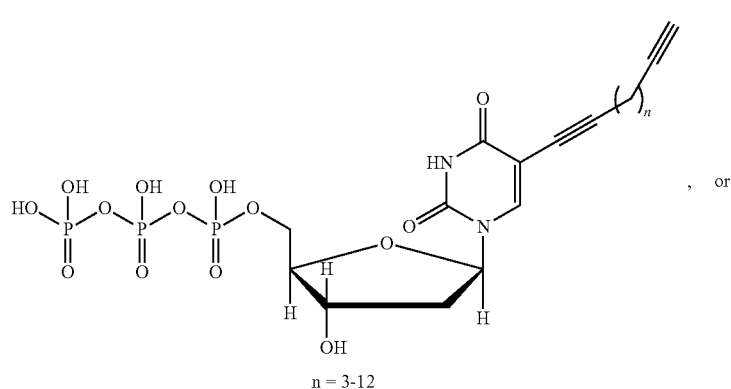

7 n = 3-12

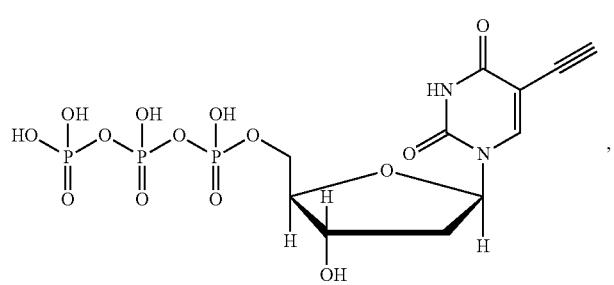

8

The reactive group can be linked to the redox label through a carbon chain or ethylene oxide (PEG) chain (see Examples of "click"-modified redox labels below).

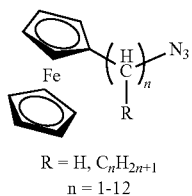

9

R = H, $C_nH_{2n+1}$
n = 1-12

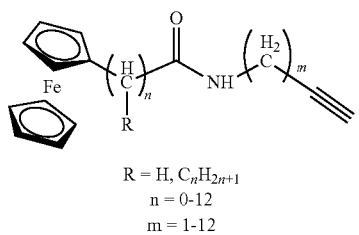

10

R = H, $C_nH_{2n+1}$
n = 0-12
m = 1-12

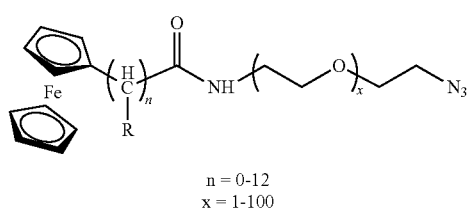

11 n = 0-12
x = 1-100

-continued

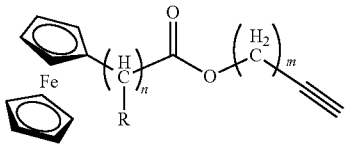

12

R = H, $C_nH_{2n+1}$
n = 0-12
m = 1-12

Although the examples provided above show a nucleotide modified at the base, a redox label or a handle can also be attached to the pentose. These examples are also shown in Verma Sandeep, and Fritz Eckstein. "Modified oligonucleotides: synthesis and strategy for users." (1998): 99-134, which is incorporated in its entirety by reference.

In an alternative embodiment, the nucleotides themselves are reporters by monitoring the change in the tunneling current between the biased electrodes. The chemistry of the nucleotide entering the polymerase and the change in the enzymatic structure upon nucleotide entering the binding pocket would cause a chemical shift in the tunneling efficiency resulting in a change in the tunneling current that would be used to differentiate the base present. An alternative modification of the DNA to enhance the change in tunneling efficiency can be used to enhance the signal, for example using a polymeric backbone (PNA) rather than a deoxyribose backbone (DNA) as the uncharged backbone would be a more significant change to the electric field vs a standard base. Other chemistries can also be used with the ultimate aim to maximize the disruption to the tunneling current when the base enters the sensing zone.

In other embodiments, the frontend of the electronics can be laid out in a fully differential way. When current is flowing into one electrode of the frontend, a current with the same amplitude, but different polarity is flowing into the second input electrode of the frontend. This avoids disturbances that couple into both electrodes from being transmitted through the signal path. Secondly a high-pass characteristic can be integrated in the very first stage of the frontend. This will avoid that differential DC currents (from tunneling or currents flowing via the polymerase) will overload the signal path of the frontend. In other words, it will avoid that the signal gets pushed to the limits of the measurement range because of those "parasitic" DC currents. The change in current from the base that needs to be detected would be transmitted via the high-pass and processed in the electronic signal chain.

The methods of various embodiments also include sequencing RNA. RNA could be processed upstream with a Reverse Transcriptase (RT) enzyme to generate cDNA that can be subsequently read using an immobilized DNA polymerase. Alternatively, the RT enzyme can be immobilized to the surface and as the RNA sequence is replicated the incorporation of redox modified dNTPs by the RT enzyme would be used to determine the original RNA template.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in an executable software object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the present disclosure that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A method for nucleic acid sequencing, the method comprising the steps of:
providing at least one device including:
an oxidizing electrode,
a reducing electrode,
a dielectric member positioned between the oxidizing electrode and reducing electrode, wherein dielectric member separates the reducing electrode from the oxidizing electrode by a first distance of at most 10 nm, and
a protein attached to a surface of the dielectric member, the protein capable of translocating a polynucleotide strand having a modified nucleotide with a redox label covalently bonded to the nucleoside base of the modified nucleotide or,
wherein the oxidizing electrode and the reducing electrode generate an electric field extending to a reaction area where the translocation of the polynucleotide strand through the protein occurs;
directing current through the oxidizing electrode and the reducing electrode, wherein the oxidizing electrode and the reducing electrode each have a length of 50 nm to 5,000 nm and a width of 10 nm to 1,000 nm in contact with a sample including the polynucleotide strand;
exposing the protein to a sample including the polynucleotide strand, wherein the polynucleotide strand is translocated through the protein; and
detecting changes in current flow in the oxidizing electrode and the reducing electrode, wherein the changes identify electron transfer from the reducing electrode, to redox label, and to oxidizing electrode when the modified nucleotide with a redox label covalently bonded to the nucleoside base of the modified nucleotide of the polynucleotide strand is at the reaction area.

2. The method of claim 1, wherein the protein is one of a DNA polymerase, RNA polymerase, ribosome, a single-stranded binding protein, topoisomerase, helicase, nuclease, exonuclease, endonuclease, a zinc finger nuclease, an RNA guided DNA endonuclease, a transcription activator-like effector nuclease, and a CRISPR protein.

3. The method of claim 1, wherein the at least one device is a plurality of devices.

4. The method of claim 3, wherein proteins in the plurality of devices are at least partially aligned on surfaces of dielectric members in the proteins in the plurality of devices.

5. The method of claim 3, wherein proteins in the plurality of devices are selected the group consisting of from a DNA polymerase, RNA polymerase, ribosome, a single-stranded binding protein, topoisomerase, helicase, nuclease, exonuclease, endonuclease, a zinc finger nuclease, an RNA guided DNA endonuclease, a transcription activator-like effector nuclease, a CRISPR protein, and combinations thereof.

6. The method of claim 1, wherein the dielectric member includes a material having a dielectric constant such that fluctuations in a tunnel current between the oxidizing electrode and reducing electrode are less than the changes in current flow resulting from the electron transfer from the reducing electrode, to redox label, and to oxidizing electrode.

7. The method of claim 6, wherein the material is at least one of aluminum oxide, titanium dioxide, hafnium oxide, zirconium oxide, silicon dioxide, silicon nitride, and hexagonal boron nitride.

8. The method of claim 1, wherein the dielectric member has a width between the oxidizing electrode and reducing electrode ranging from 1 nm to 10 nm.

9. The method of claim 1, wherein voltages of the oxidizing and reducing electrodes in the directing step are different from each other.

10. The method of claim 1, wherein the modified nucleotide with a redox label covalently bonded to the nucleoside base of the modified nucleotide has the following formula:

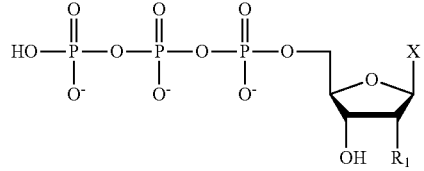

wherein:
X is

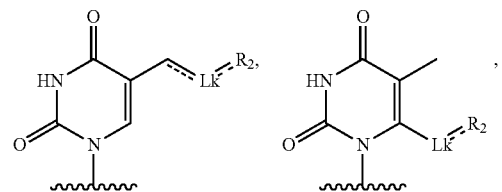

-continued

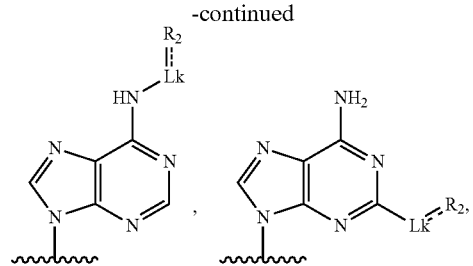

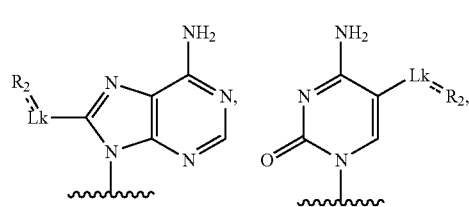

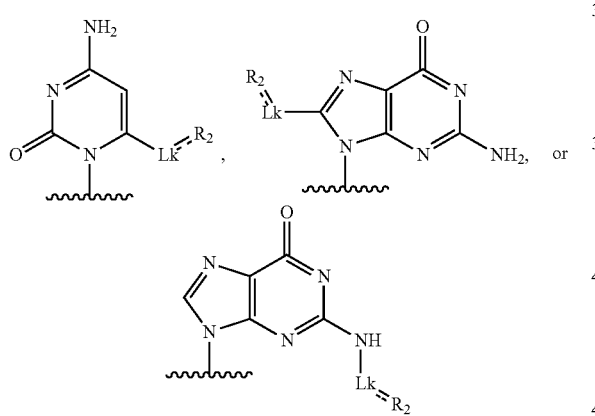

is a single bond, a double bond, a triple bond,
Lk is absent or a hydrocarbon-containing linking group including an alkyl, aryl, heteroalkyl, heteroaryl, cycloalkyl, or heteroatom-containing ring system,
$R_1$ is H, or OH, and
$R_2$ is a redox label.

11. The method of claim 1, wherein the modified nucleotide with a redox label covalently bonded to the nucleoside base of the modified nucleotide has the following formula:

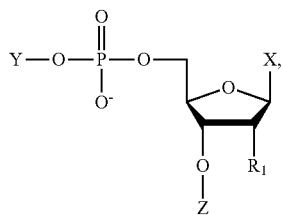

wherein:
Y is a ribose, deoxyribose, or H,
Z is a phosphate or hydrogen,
X is

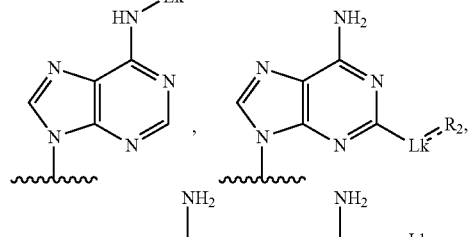

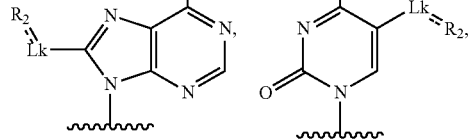

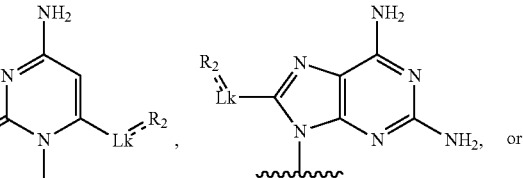

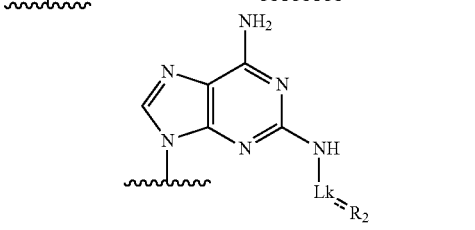

is a single bond, a double bond, a triple bond,
Lk is absent or a hydrocarbon-containing linking group including an alkyl, aryl, heteroalkyl, heteroaryl, cycloalkyl, or heteroatom-containing ring system,
$R_1$ is H or OH, and
$R_2$ is a redox label.

12. A system for nucleic acid sequencing comprising:
at least one device including
an oxidizing electrode,
a reducing electrode,
a dielectric member positioned between the oxidizing electrode and reducing electrode, wherein dielectric member separates the reducing electrode from the oxidizing electrode by a first distance of at most 10 nm, and wherein the oxidizing electrode and the reducing electrode each have a length of 50 nm to 5,000 nm and a width of 10 nm to 1,000 nm in contact with a sample including a polynucleotide strand, and
a protein attached to a surface of the dielectric member, the protein being capable of translocating a polynucleotide strand having a nucleotide modified with a redox label covalently bonded to the nucleoside base of the modified nucleotide or;

wherein the oxidizing electrode and the reducing electrode generate an electric field extending to a reaction area where the translocation of the polynucleotide strand through the protein occurs;

wherein electron transfer from the reducing electrode, to redox label, and to oxidizing electrode occurs when the modified nucleotide with a redox label covalently bonded to the nucleoside base of the modified nucleotide is located at the reaction area.

13. The system of claim 12, wherein the protein is one of a DNA polymerase, RNA polymerase, ribosome, a single-stranded binding protein, topoisomerase, helicase, nuclease, exonuclease, endonuclease, a zinc finger nuclease, an RNA guided DNA endonuclease, a transcription activator-like effector nuclease, and a CRISPR protein.

14. The system of claim 12, wherein the dielectric member includes at least one of silicon dioxide, silicon nitride, and aluminum oxide, titanium dioxide, hafnium oxide, zirconium oxide, and hexagonal boron nitride.

15. The system of claim 12, wherein the dielectric member has a width between the oxidizing and reducing electrodes ranging from 1 nm to 10 nm.

16. The system of claim 12, wherein the modified nucleotide with a redox label covalently bonded to the nucleoside base of the modified nucleotide has the following formula:

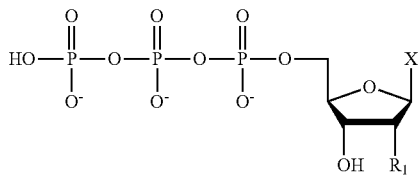

wherein:
X is

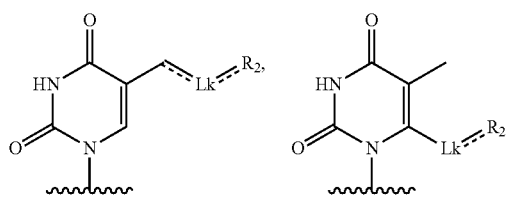

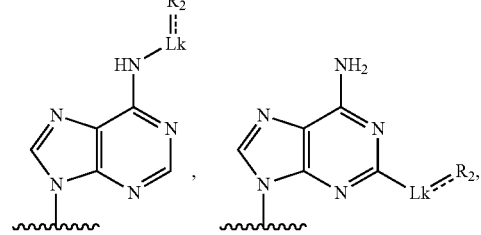

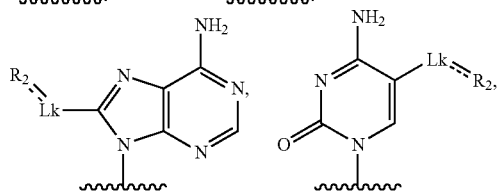

-continued

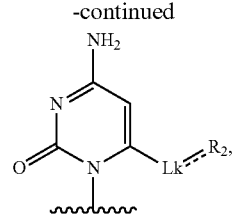

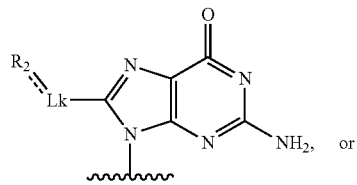

or

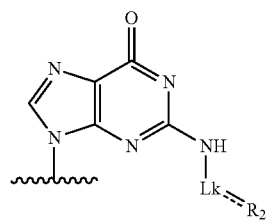

is a single bond, a double bond, a triple bond,

Lk is absent or a hydrocarbon-containing linking group including an alkyl, aryl, heteroalkyl, heteroaryl, cycloalkyl, or heteroatom-containing ring system, $R_1$ is H or OH, and $R_2$ is a redox label.

17. The system of claim 12, wherein the modified nucleotide with a redox label covalently bonded to the nucleoside base of the modified nucleotide has the following formula:

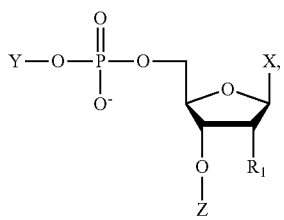

wherein:
Y is a ribose, deoxyribose, or H,
Z is a phosphate or hydrogen,
X is

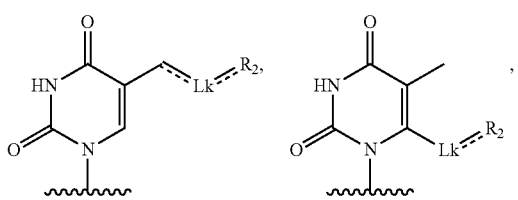

——— is a single bond, a double bond, a triple bond,
Lk is absent or a hydrocarbon-containing linking group including an alkyl, aryl, heteroalkyl, heteroaryl, cycloalkyl, or heteroatom-containing ring system,
$R_1$ is H or OH, and
$R_2$ is a redox label.

18. The system of claim 12 further comprising an array including a plurality of the devices.

19. The system of claim 18, wherein proteins in the plurality of the devices are at least partially aligned on surfaces of dielectric members in the plurality of the devices.

20. The system of claim 18, wherein proteins in the plurality of the devices are selected from the group consisting of a DNA polymerase, RNA polymerase, ribosome, a single-stranded binding protein, topoisomerase, helicase, nuclease, exonuclease, endonuclease, a zinc finger nuclease, an RNA guided DNA endonuclease, a transcription activator-like effector nuclease, a CRISPR protein, and combinations thereof.

21. A method for forming a device for nucleic acid sequencing, the method comprising the steps:
providing a device including an oxidizing electrode, a reducing electrode, a dielectric member positioned between the oxidizing electrode and reducing electrode, wherein dielectric member separates the reducing electrode from the oxidizing electrode by a first distance of at most 10 nm, and wherein the oxidizing electrode and the reducing electrode each have a length of 50 nm to 5,000 nm and a width of 10 nm to 1,000 nm in contact with a sample including a polynucleotide strand;
generating an electric field by the oxidizing electrode, the reducing electrode, or both; and
attaching a protein to a surface of the dielectric member, the protein being capable of translocating a polynucleotide strand having a nucleotide modified with a redox label covalently bonded to the nucleoside base of the modified nucleotide, wherein the protein is one of a nuclease and a CRISPR protein.

22. The method of claim 21, wherein:
the providing step further includes providing an array having a plurality of the devices;
the generating step further includes generating an electric field by each oxidizing electrode, each reducing electrode, or both; and
the attaching step further includes attaching a protein capable of translocating a polynucleotide strand having a nucleotide modified with a redox label covalently bonded to the nucleoside base of the modified nucleotide or capable of receiving the modified nucleotide with a redox label covalently bonded to the nucleoside base of the modified nucleotide to a surface of each dielectric member such that the proteins are at least partially aligned on surfaces of dielectric members in the plurality of the devices.

* * * * *

SEQUENCE LISTING

```
<160> NUMBER OF SEQ ID NOS: 4

<210> SEQ ID NO 1
<211> LENGTH: 38
<212> TYPE: DNA
<213> ORGANISM: Unknown
<220> FEATURE:
<223> OTHER INFORMATION: Illustrative example of an embodiment of the
      invention

<400> SEQUENCE: 1
atcccggctt aagagaccgt tggtgacctg aacgctaa                              38

<210> SEQ ID NO 2
<211> LENGTH: 26
<212> TYPE: DNA
<213> ORGANISM: Unknown
<220> FEATURE:
<223> OTHER INFORMATION: Illustrative example of an embodiment of the
      invention

<400> SEQUENCE: 2
ttagcgttca ggtcaccaac ggtctc                                           26

<210> SEQ ID NO 3
<211> LENGTH: 38
<212> TYPE: DNA
<213> ORGANISM: Unknown
<220> FEATURE:
<223> OTHER INFORMATION: Illustrative example of an embodiment of the
      invention
```

```
<400> SEQUENCE: 3
atcccggctt ccgagaccgt tggtgacctg aacgctaa                           38

<210> SEQ ID NO 4
<211> LENGTH: 27
<212> TYPE: DNA
<213> ORGANISM: Unknown
<220> FEATURE:
<223> OTHER INFORMATION: Illustrative example of an embodiment of the
      invention

<400> SEQUENCE: 4
ttagcgttca ggtcaccaac ggtctcg                                       27
```